United States Patent [19]
Goodnow, Jr. et al.

[11] Patent Number: 5,780,607
[45] Date of Patent: Jul. 14, 1998

[54] ANTISENSE OLIGOMERS

[75] Inventors: Robert Alan Goodnow, Jr., Basking Ridge; Steve Yik-Kai Tam, West Caldwell, both of N.J.

[73] Assignee: Hoffmann-La Roche Inc., Nutley, N.J.

[21] Appl. No.: 727,685

[22] Filed: Oct. 8, 1996

Related U.S. Application Data

[60] Provisional application Nos. 60/002,484 Aug. 9, 1996 and 60/005,689 Oct. 13, 1995.

[51] Int. Cl.$^6$ .......................... C07H 19/00; C07H 21/04
[52] U.S. Cl. .......................... 536/22.1; 536/24.3
[58] Field of Search ........................ 536/22.1, 24.3

[56] References Cited

U.S. PATENT DOCUMENTS 4,395,406  7/1983  Gacek et al. .......................... 424/180

FOREIGN PATENT DOCUMENTS 2646676   4/1977   Denmark.
WO 95/20597  8/1995   WIPO.

OTHER PUBLICATIONS

Stein et al. "Antisense Oligonucleotides as Therapeutic Agents–Is the Bullet Really Magical?" Science, vol. 261, pp. 1004–1012, 1993.
Zamecnik, P.C.; Stephenson, M.L. Proc.Natl.Acad.Sci USA 1978, 75 pp. 280–284.
Stein, C.A.;Narayanan, R.Current Opinion in Oncology, vol. 6, pp. 587–594.
Branda,R.F.;Moore, A.L.; Mathews,L.; McCormack,J.J.; Zon, G. Biochem.Pharmacol. 1993, 8, pp. 2037–2043.
McIntyre,K.W. et al. Antisense Res. Devel. 1993, 3, pp. 309–322.
Giles, R.V.; Spiller, D.G.;Tidd D.M. Anticancer Drug Design,1993,8, pp. 33–51.
Milligan,J.F.;Matteucci;Martin,J.C., J. Med.Chem. 1993, 36, pp. 1923–1937.
Burgess, K.;Gibbs,R.A.;;Metzker,M.L.;Raghavachari,R.J. J.C.S.Chem.Commun. 1994, pp. 915–916.
Chur A.; Holst, B.; Dahl, O., Valentin–Hansen, P.; Pedersen, E.B. Nucleic Acid Res. 1993, 21, pp. 5179–5183.
Idziak,I.; Just G.; Damha, M.; Giannaris, P. Tet. Lett. 1993, 34, pp. 5417–5420.
De Mesmaeker, A.; Waldner, A.; Lebreton, J; Hoffmann, P.; Fritsch, V.; Wolf, R.; Freier, S. Angew. Chem. Intl. Ed. Engl. 1994; 33, 226–229.
Nielson, P.; Egholm, M.; Berg, R.; Buchardt, O. Science, 1991, 254, pp. 1497–1500.
Akhtar and Ivinson, Nature Genetics, 1993, 4, pp. 215–217.
Müller, G.; Ruppert, S.; Schmid, E.; Schütz, G. EMBO, 1988, 7, pp. 2723–2730.
Ando S.; Ando O.; Suemoto, Y.; Mishima, Y.J. Invest. Dermatol.1993, 100, pp. 150S–155S.
Kuzumaki, T.; Matsuda, A.; Wakamatsu, K.; Ito, S.; Ishikawa, K. Expt.Cell Res. 1993, 207, pp. 33–40.
Fields, G. and Noble, R. Int. J. Peptide Protein Res. 1990, 35, pp. 161–214.
Koerber, S.C.; Fink, A.L.; Analytical Biochemistry 1987, 165, pp. 75–87.
Petersheim, J.;Turner, D.H. Biochemistry 1983, 22, pp. 256–263.
Bradford, M.M. Anal. Biochem. 1976, 72 pp. 248–255.
Pomerantz, S.H. J. Biol. Chem. 1966, 241, pp. 161–168.
Mosmann, T.J. Immunol. Meth. 1983, 65, pp. 55–63.
Egholm et al. Nucleic Acids Research 23:217 (1995).
Carbohydrate Modifications in Antisense Research, vol. 6, pp. 81–99 (1994).
Pravdic et al., Carbohydr. Res., 62, 1978, pp. 301–312.
Jeanloz and Garg, Carbohydr. Res. 62, 1978, pp. 185–190.
Nakazaki et al., Carbohydr. Res. 44, 1975, pp. 215–226.
Wolfrom et al., Carbohydr. Res. 20, 1971, pp. 375–381.

(List continued on next page.)

*Primary Examiner*—Ardin H. Marschel
*Assistant Examiner*—Jezia Riley
*Attorney, Agent, or Firm*—George W. Johnston; Dennis P. Tramaloni; Joseph P. Kirk, Jr.

[57] ABSTRACT

Antisense oligomers of the formula

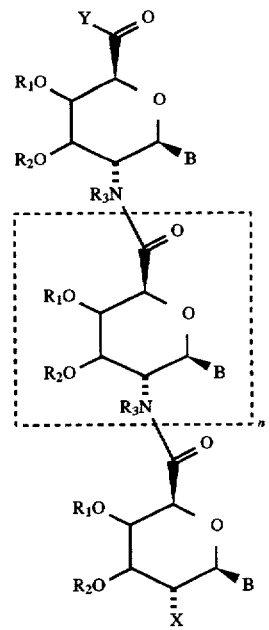

wherein
$R_1$, $R_2$ and $R_4$ are independently hydrogen, lower alkyl or acyl;
$R_3$ is hydrogen or lower alkyl;
B is a nucleobase or a protected nucleobase, such that said oligomer has a sequence of bases complementary to a selected RNA;
n is 5 to 30;
X is $NR_3R_4$;
Y is $OR_3$, or $NHR_3$;
as well as, pharmaceutically acceptable salts thereof.

17 Claims, No Drawings

OTHER PUBLICATIONS

Wolfrom et al., Carbohydr. Res. 11, 1969, pp. 63–76.
Wolfrom et al., J. Org. Chem. 32, 1967, pp. 1821–1823.
Covill et al. Tetrahedr. Lett. 9, 1968, pp. 1033–1034.
Wolfrom et al., J. Org. Chem. 32, 1967, pp. 653–655.
Wolfrom et al. J. Org. Chem. 33, 1968, pp. 4227–4231.
Wolfrom et al. J. Org. Chem. 32, 1967, pp. 2757–2758.
Idegami et al. Chem. Pharm. Bull. 38, 1990, pp. 1766–1768.
Chemical Abstracts, 110(3), 1989, Abstr. No. 24206, p. 585.
Augustyns et al. Nucleic Acids Res. 20, 1992, pp. 4711–4716.

ANTISENSE OLIGOMERS

This application claims the benefit of Provisional application Ser. No. 60/005,689, filed Oct. 13, 1995, and Provisional application Ser. No. 60/022,484, filed Aug. 9, 1996.

BACKGROUND OF THE INVENTION

The highly specific interaction between synthetic oligonucleotides and RNA or single-stranded DNA has led to many applications in molecular biology. Oligonucleotides are used as hybridization probes for cloning, diagnostic assays, and as indispensable primer reagents in the polymerase chain reaction (PCR) technology. The specificity of binding is governed by the Watson Crick base-pairing rule. This feature allows the design of an oligonucleotide reagent to be fairly straightforward, requiring only a knowledge of the target RNA or DNA sequence. As a further extension of this attractive principle, binding of an oligonucleotide with its complementary mRNA sequence has been studied as a new tool for inhibiting the translation process of a specific protein product. In 1978, Zamecnik and Stephenson demonstrated the usefulness of the approach in the inhibition of Rous Sarcoma Virus development in infected chicken fibroblasts (Zamecnik, P. C.; Stephenson, M. L. *Proc. Natl Acad. Sci. U.S.A.* 1978 75, 280). This pioneering work has led to a blossoming of studies in the field and generated enormous interest in developing this concept for therapeutic applications. Since the oligonucleotide agent used is complementary (anti) to the sense of the genetic message contained in the mRNA target, this new approach was dubbed "antisense DNA" technology.

Phosphorothioates are widely known antisense compounds. These are backbone analogs in which one oxygen in the phosphodiester group is replaced by a sulfur atom. This conservative modification renders the molecules nuclease resistant and allows them to exhibit biological activities in cell cultures and in animal models. Phosphorothioate antisense drugs have entered clinical trials for evaluation as antiviral or anticancer agents.

However, while the potential of phosphorothioate antisense drugs remains promising, there is a need for new types of antisense agents due to side effects. Specifically, non-antisense side activities are exhibited by the phosphorothioates because their polythioate backbones are ionic. These side activities affect protein binding (Stein, C. A.; Narayanan, R. *Current Opinion in Oncology*, Vol. 6, No. 6, pgs. 587–94 (1994)), activation of immune cells and transcription factor(s) (Branda, R. F.; Moore, A. L.; Mathews, L.; McCormack, J. J.; Zon, G. *Biochem. Pharmacol.* 1993, 8, 33; and McIntyre, K. W. et al. *Antisense Res. Devel*, 1993, 3, 309), and RNase H cleavage of non-target sequences due to partial complementary binding (Giles, R. V.; Spiller, D. G.; Tidd, D. M. *Anticancer Drug Design* 1993, 8, 33).

To reduce non-antisense activities due to ionic backbones, oligonucleotides incorporating a few modified residues have been synthesized (Milligan, J. F.; Matteucci, M. D.; Martin, J. C. *J. Med. Chem.* 1993, 36, 1923 and *Carbohydrate Modifications in Antisense Research*: Sanghvi, Y. S.; Cook, P. D. Eds.; ACS: Washington, D.C. (1994)). Specifically, residues in which the phosphodiester linkage has been replaced with an amide have been synthesized (Burgess, K.; Gibbs, R. A.; Metzker, M. L.; Raghavachari, R J. C. S. *Chem. Commun.* 1994, 915; Chur, A.; Holst, B.; Dahl, O.; Valentin-Hansen, P.; Pedersen, E. B. *Nucleic Acid Res.* 1993, 21, 5179; Idziak, I.; Just, G.; Damha, M.; Giannaris, P. *Tet. Lett.* 1993, 34, 5417; De Mesmaeker,A.; Waldner, A.; Lebreton, J.; Hoffmann, P.; Fritsch, V.; Wolf, R.; Freier, S. *Angew. Chem. Intl. Ed.* Engl. 1994, 33, 226). Incorporation of these modified linkages into a single stranded DNA molecule usually results in a lowering of binding affinity with either a complementary RNA or DNA. However, no example of a total replacement of the phosphodiester groups by amide groups has been reported.

Another type of analog with higher binding affinity is the Peptide Nucleic Acid (PNA) (Nielsen, P.; Egholm, M.; Berg, R.; Buchardt, O. *Science*, 1991, 254, 1497). These molecules contain the familiar nucleic acid bases —adenine, guanine, thymine and cytosine—linked to a peptide backbone rather than the sugar-phosphate backbone. Although this type of compound has high binding affinity with DNA and RNA, this type of compound also shows poor specificity by binding to antiparallel as well as to parallel complementary sequences of RNAs. Moreover, the poor water solubility of these molecules has become a drawback to their practical application.

Thus, there is a need for an antisense molecule with a backbone linkage having several characteristics, namely the linkage should be stable to enzymatic cleavage, should be neutral to avoid side effects associated with polyanionic structures, should have acceptable affinity and specificity in its binding with RNA, and should have a desirable physical chemical properties, for example, water solubility. The antisense molecules of this invention meet these requirements. In contrast to existing art, antisense molecules of this invention are a new class of oligoribonucleotides comprising pyranosyl nucleoside building blocks connected by amide linkages. Oligomers of formula I bind to DNA and RNA with strong affinity and base sequence selectivity. The water soluble oligomers of formula I are stable to extremes in acidity and basicity and to the enzymes found in blood serum.

SUMMARY OF THE INVENTION

This invention is directed to a new type of oligomer which is composed of pyranosyl nucleoside monomer units connecting by amide linkages. Synthesis of these compounds can be achieved by oligomerization of monomeric intermediates which are also part of this invention, using for example solid phase or solution coupling methodology. Due to the specific structures of this invention, the antisense molecules disclosed herein have the advantages of stability and water solubility, and avoid side effects and nonspecific protein binding associated with phosphorothioates.

Accordingly, the invention relates to an oligomer of formula

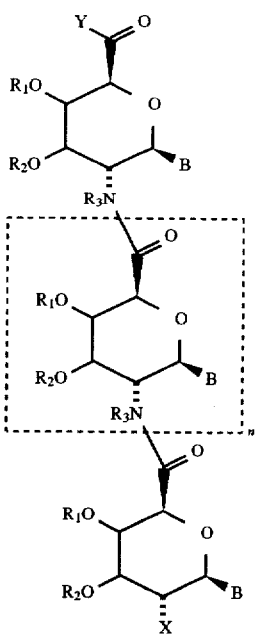

wherein

R$_1$, R$_2$ and R$_4$ are independently hydrogen, lower alkyl or acyl;

R$_3$ is hydrogen or lower alkyl;

B is a nucleobase or a protected nucleobase, such that said oligomer has a sequence of bases complementary to a selected RNA sequence;

n is 5 to 30;

X is NR$_3$R$_4$;

Y is OR$_3$, or NHR$_3$;

as well as, pharmaceutically acceptable salts thereof.

The invention is also directed to monomeric building blocks of formula

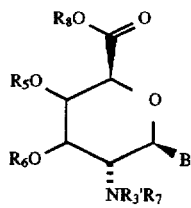

wherein R$_5$ and R$_6$ are independently hydrogen or a hydroxy protecting group or R$_5$ and R$_6$ taken together are a 1,2-dihydroxy protecting group, for example a ketal; R$_3$' is hydrogen or lower alkyl; R$_7$ is hydrogen or an amine protecting group; R$_8$ is hydrogen or an acid protecting group; and B is a nucleobase or protected nucleobase, such as N-benzoyl- or N-acetylcytosine, N-benzoyladenine, N,N-dibenzoyladenine, or N-acetyl or N-isobutyrylguanine.

The invention includes pharmaceutical compositions which decrease the production of a target protein in a cell, which have as the active ingredient a compound of formula I in an amount effective to bind to the mRNA encoding the target protein and by this binding decrease production of the protein, and a pharmaceutically acceptable carrier.

DETAILED DESCRIPTION OF THE INVENTION

The invention is directed to an oligomer of formula I which is composed of pyranosyl nucleoside monomer units connected by amide linkages. The oligomers of this invention are useful in any application involving antisense nucleotides. In particular, the oligomer of formula I has enhanced enzymatic and chemical stability and water solubility over oligomers with modified linkages of other types while retaining binding sequence specificity to target mRNA. In addition, it is possible by means of this invention to obtain oligomers all of whose component nucleosides are connected by amide linkages.

Because of their amide linkage, the present oligomers can be assembled into antisense compounds which are stable, water soluble, and in particular nuclease resistant. Thus, the oligomers of this invention are useful as antisense therapeutics which bind to a target mRNA to block or decrease the production of a target protein. Antisense therapeutics are used as described in Akhtar and Ivinson, *Nature Genetics*, 1993 4, 215. As an example of designing an antisense oligomer, a target protein may be selected which causes or contributes to an undesirable condition. The nucleotide sequence of the gene or mRNA corresponding to the protein is then obtained by known methods, and oligomers complementary to part of this sequence may then be designed. A preferred size for such oligomers is in the range of about 2 to about 28, especially about 7 to about 22 monomers (n=5 to 20).

These antisense oligomers, when made by the method of this invention as provided below form stable antisense compounds which may then be administered to alleviate the condition associated with the presence of the target protein. The oligomers of this invention are especially useful as antisense compounds for treatment of conditions related to the production of undesired or excessive proteins whether native or foreign, and are also useful to block the proliferation of viruses or cancer cells. Antisense oligomers are designed to be complementary to the mRNA of a target gene, and bind to the RNA to prevent its translation, consequently reducing or preventing synthesis of the protein encoded by the target gene. Therefore, the ability to bind stably to nucleic acid under physiological conditions indicates antisense utility. In addition, an antisense compound must have appropriate sequence binding specificity in order to bind to the specific mRNAs of a target gene. Finally, antisense compounds must be sufficiently soluble to be physiologically effective and reach the target mRNA. These oligomers are also useful as PCR clamps for use in PCR technology, and have the advantage of stable and specific binding in PCR, and are also useful as probes in diagnostic tests employing nucleic acid hybridization. (See, for example, *Nucleic Acids Research* 23:217, 1995).

The carboxy and amino terminal residues of the oligomers of this invention may be modified in any conventional way to make the compound more compatible with solid phase synthesis or to confer desirable physical chemical properties.

A specific application for the oligomers with linkages of this invention is in the antisense treatment of hyperpigmentation. Hyperpigmentation results from overproduction of the enzyme tyrosinase in melanocytes (pigment cells). Adding an oligomer of this invention which has the sequence corresponding to relevant portions of the mRNA encoding tyrosinase (Müller, G.; Ruppert, S.; Schmid, E.; Schütz, G. *EMBO* 1988, 7, 2723–30) inhibits tyrosinase production, thus eliminating hyperpigmentation in affected cells (Ando, S.; Ando, O.; Suemoto, Y.; Mishima, Y. *J. Invest. Dermatol.* 1993,100, 1505–1555) (Kuzumaki, T.; Matsuda, A.; Wakamatsu, K.; Ito, S.; Ishikawa, K. *Expt. Cell Res.* 1993, 207, 33–40). The efficacy of an antisense oligomer for reducing hyperpigmentation may be determined using a cell-based antisense assay, for example the assay of Example 1.

As used herein, the term "lower alkyl" denotes an alkyl group containing 1 to 4 carbon atoms, for example, methyl, ethyl, propyl, isopropyl, butyl, and the like, preferably methyl or ethyl. The term "acyl" denotes an organic radical derived from an organic acid by removal of a hydroxyl group, for example; an aliphatic acid such as acetic acid, propionic acid, isobutyric acid, stearic acid, oleic acid, palmitolic acid and the like; an aromatic acid such as benzoic acid or substituted benzoic acid; a heteroaromatic acid, preferably comprising a 5 to 6 membered ring containing at least one of the heteroatoms, S or N, such as 2-furan-carboxylic acid or 2-pyridine-carboxylic acid. By lower alkanol is meant hydroxy substituted lower alkyl such as hydroxy ethyl or hydroxypropyl. The term "aryl" denotes a group derived from an aromatic hydrocarbon which may be substituted or unsubstituted such as phenyl, para-nitrophenyl, para-bromophenyl, para-chlorophenyl, para-methylphenyl and para-methoxyphenyl and the like. By aralkyl is meant aryl substituted alkyl, such as benzyl and the like.

The term "hydroxy protecting group" means any conventional hydroxy protecting group known in the art. Exemplary of such hydroxy protecting groups are lower alkyl, acyl, lower alkanol, aryl, aralkyl, trimethylsilyl ether, triethylsilyl ether, isopropyldimethylsilyl ether, tert-butyldimethylsilyl ether and the like.

The term "amine protecting group" means any conventional amine protecting group such as, for example, 9-fluoroenylmethoxycarbonyl (F-moc), tert-butyloxycarbonyl (t-Boc), benzyloxycarbonyl, allyloxy carbonyl, triphenylmethyl and 4,4'-dimethyloxytrityl (DMT), preferably Fmoc and t-Boc.

The term "acid protecting group" means any conventional acid protecting group known in the art. Exemplary of such acid protecting groups are lower alkyl, benzyl, phenyl, 2-trimethylsilyl-ethyl, preferably benzyl or tert-butyl.

The nucleobases may include any combination of the known natural or modified nucleobases. Preferred nucleobases are the natural ones, such as, adenine, cytosine, guanine, thymine, and uracil. Modified bases which are known in the art, such as, 5-(1-propynyl)uracil, 5-(1-propynyl)cytosine, inosine, 5-methylcytosine and 2,6-diaminopurine may be used. The sequence of bases for an antisense oligomer is selected such that the oligomer presents a base sequence that is complementary to a selected mRNA. As noted above, the mRNA sequence may be determined on the basis that the mRNA encodes a protein whose translation is desired to be blocked in order to reduce or eliminate production of that protein to alleviate undesired effects caused in a subject by the presence of the protein. mRNA sequences which are not already known may be determined by translating the sequence of the encoded protein using the genetic code. If the protein sequence is not known, then it may be determined by isolating and sequencing the protein by known techniques. Alternatively, the mRNA or DNA encoding the protein may be identified, isolated, and sequenced by known methods.

The term protected nucleobase means a base as defined above which is protected by a conventional nucleoside protecting group known in the art. Examples of a protected nucleobase include N-benzoyl- or N-acetylcytosine, N-benzoyladenine, N,N-dibenzoyladenine, or N-acetyl-or N-isobutyrylguanine.

In the formulas presented herein, the various substituents are illustrated as joined to the nucleus by one of the following notations: a wedged solid line (—■) indicating a substituent which is above the plane of the molecule (β-orientation) and a wedged dotted line (⋯⋯) indicating a substituent which is below the plane of the molecule (α-orientation).

Accordingly, the present invention encompasses all four combinations of isomers at the C-3 and C-4 positions of carbohydrates, as illustrated below in formulas Ia–Id and IIa–IId. The isomers of formulas Ia and IIa are preferred.

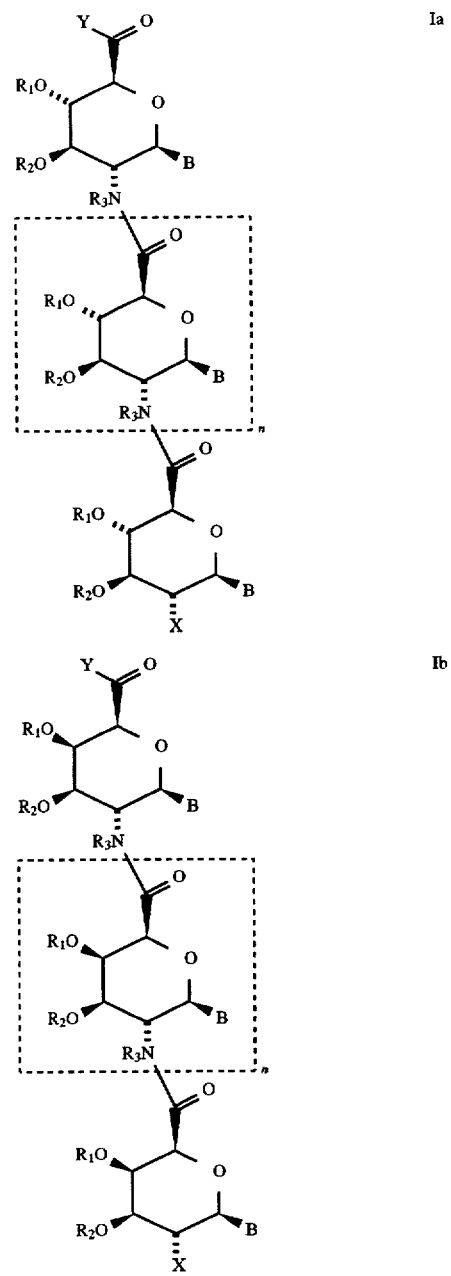

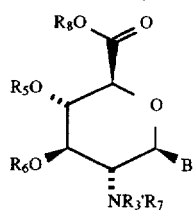

Formula Ia and Formula IIa gluco configuration

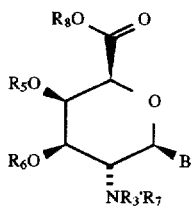

Formula Ib and Formula IIb galacto configuration

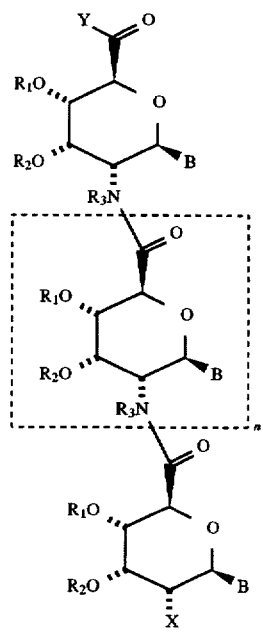

Ic

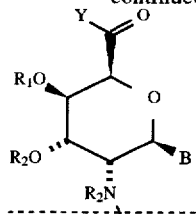

Id

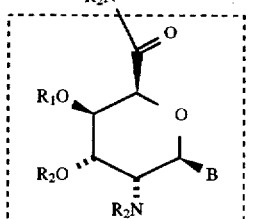

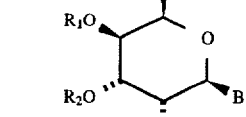

Formula Ic and Formula IIc allo configuration

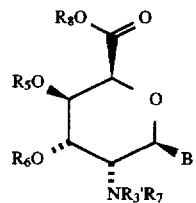

Formula Id and Formula IId gulo configuration

In a preferred embodiment of the oligomer of formula I, $R_1$ and $R_2$ are independently hydrogen, methyl, ethyl or acetyl. $R_3$ is hydrogen or methyl. B is thymine, cytosine, adenine, guanine, uracil, N-benzoylcytosine, N-acetylcytosine, N-benzoyladenine, N,N-dibenzoyladenine, N-acetylguanine or N-isobutyrylguanine; n is 5 to 20; X is $NH_2$ or NHAc wherein Ac is acetyl; Y is $OCH_3$, $NH_2$ or $NHCH_3$.

In a particularly preferred embodiment, $R_1$ and $R_2$ are independently hydrogen, or acetyl, X is $NH_2$; Y is hydroxy or $NH_2$; $R_3$ is hydrogen or $CH_3$; n is 5–15 and B is thymine, cytosine adenine, guanine or uracil.

Once the target base sequence is known, the antisense oligomers of this invention may be prepared accordingly using intermediates of this invention. These intermediates are prepared and then appropriately linked together by the method below, which is also part of this invention. The RNA binding property of the oligomer may be determined by conventional thermal melting techniques.

The invention also relates to compounds of formula II which are monomeric building blocks in the synthesis of oligomers of formula I. In a preferred compound of formula II, $R_5$ and $R_6$ are independently hydrogen, methyl, ethyl, acetyl or trisubstituted silyl ether, such as triethylsilyl, isopropyldimethylsilyl or tert-butyldimethylsilyl. $R_3'$ is hydrogen or lower alkyl. $R_7$ is preferably 9-fluorenylmethoxycarbonyl or tert-butyloxycarbonyl. In a preferred compound of formula II, $R_8$ is hydrogen, tert-butyl or benzyl. B is preferably thymine, cytosine, adenine, guanine, uracil, N-benzoylcytosine, N-acetylcytosine, N-benzoyladenine, N,N-dibenzoyladenine, N-acetylguanine or N-isobutyrylguanine.

In a particularly preferred embodiment of the compound of formula II, $R_5$ and $R_6$ are trisubstituted silylether particularly preferred is isopropyl-dimethylsilyl. $R_3'$ is hydrogen. $R_7$ is 9-fluoroenylmethoxycarbonyl or tert-butyloxycarbonyl. $R_8$ is benzyl or hydrogen and B is thymine, uracil, N-benzoyl-cytosine, N-acetylcytosine, N-benzoyladenine, N,N-dibenzoyladenine, N-acetylguanine or N-isobutyrylguanine.

The compounds of formula II and oligomer of formula I are prepared as hereafter described in Schemes I, II, III and the Examples, Scheme I being the preferred method of making compounds of formula II.

SCHEME I

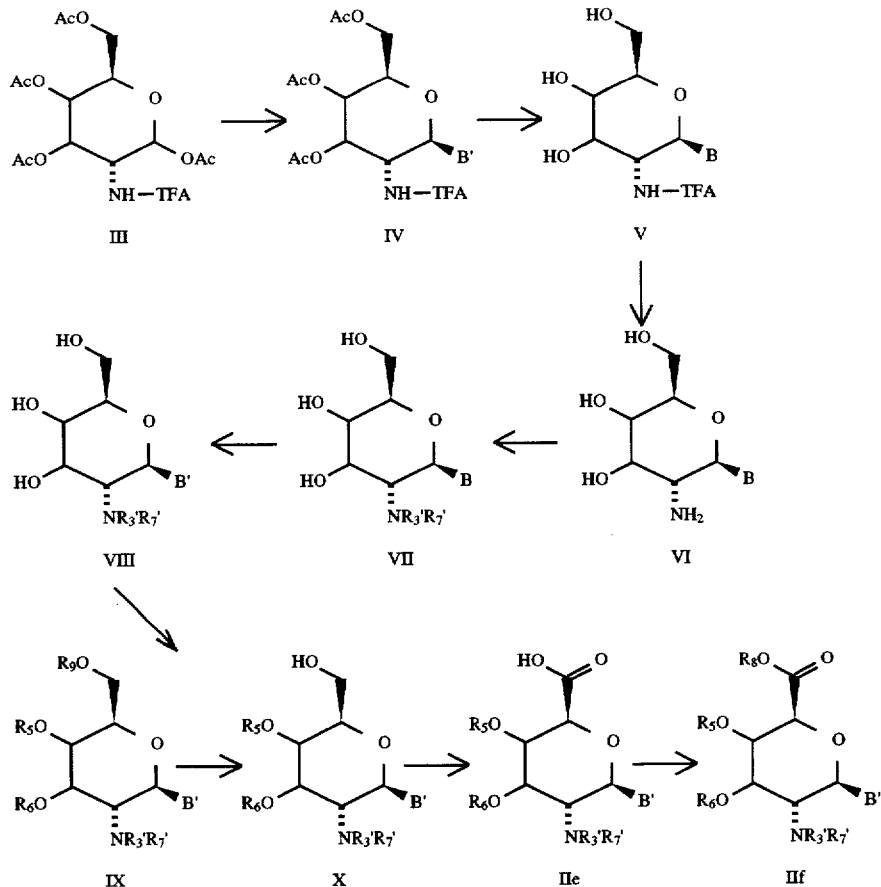

wherein B' is a protected nucleobase, $R_3'$ is hydrogen or lower alkyl, $R_7'$ is an amine protecting group, $R_8$ is an acid protecting group, $R_9$ is an alcohol protecting group which reacts preferentially with primary hydroxy groups such as tert-butyldimethylsilyl or triphenylmethyl, Ac is acetyl, TFA is trifluoroacetyl, and B, $R_5$, $R_6$ and $R_7$ are as described above.

In above Scheme I, the compound of formula III, a known compound or compound prepared by known methods, is converted to the compound of formula IV by reaction with a Lewis acid catalyst such as $SnCl_4$ or trimethylsilyl trifluoromethanesulfonate in presence of a persilylated, protected base in an anhydrous, aprotic solvent such as $CH_3CN$ or $ClCH_2CH_2Cl$ solvent at a temperature in the range of 20°–100° C., preferably at 80°–100° C.

A compound of formula IV is de-acetylated to the corresponding compound of formula V by conventional methods such as, base catalyzed hydrolysis in protic solvents, preferably a system composed of CH$_3$OH / H$_2$O / (CH$_3$CH$_2$)$_3$N. The trifluoroacetamide of formula V is hydrolyzed by conventional methods such as, reaction with a base, preferably 30% aqueous ammonium hydroxide to give the corresponding compound of formula VI.

When in formula VII R$_3$ is hydrogen, a compound of formula VI is converted to the corresponding compound of formula VII by reaction with N-(9-fluorenylmethoxycarbonyloxy)succinimide in a solvent such as aqueous dimethylformamide in the presence of NaHCO$_3$.

When in formula VII R$_3$ is lower alkyl, a compound of formula VI is converted to the corresponding compound of formula VII by reaction with 1 equivalent of an aldehyde and sodium cyanoborohydride in a polar solvent, preferably methanol, then followed by reaction with N-(9-fluorenylmethoxycarbonyloxy)succinimide in a solvent such as aqueous dimethylformamide in the presence of NaHCO$_3$.

The compound of formula VII is preferably purified by trituration with excess ether and water.

The nucleobase B in the compound of formula VII is then protected by reaction with an activated acyl donating group such as benzoic anhydride or acetyl chloride in an anhydrous solvent such as pyridine, to give the corresponding compound of formula VIII.

A compound of formula VIII is converted to the corresponding compound of formula IX by reaction with a primary hydroxy selective protecting group reagent, followed by reaction with a conventional hydroxy protecting group reagent, such as alkyl halide, acetic anhydride or trisubstituted silyl ether. The preferred method is by reaction of formula VIII with excess silylating agent, such as chlorotrialkylsilane or trialkylsilyl trifluoromethanesulfonate in the presence of a base, specifically, with an excess of both tert-butyldimethylsilyl trifluoromethanesulfonate and 2,6-lutidine or with an excess of both isopropyldimethylsilyl chloride and imidazole in an anhydrous solvent such as CH$_2$Cl$_2$.

The protecting group of the primary alcohol in a compound of formula IX is then selectively removed by conventional methods to give the corresponding compound of formula X. For example, when silyl ether is the hydroxy protecting group, this transformation can be carried out by reaction with camphor sulfonic acid in a solvent such as methanolic CH$_2$Cl$_2$.

The primary alcohol in a compound of formula Xis then oxidized to a carboxylic acid to give the corresponding compound of formula IIe for example, by reaction with aqueous NaClO solution, and 2,2,6,6-tetramethyl-1-piperidinyloxy free radical in an aprotic aqueous-immiscible solvent such as aqueous CH$_2$Cl2 followed by reaction with NaClO$_2$ in a solvent such as aqueous tert-butanol.

A compound of formula IIe is converted to the corresponding compound of formula IIf by conventional methods of adding an acid protecting group, such as, a benzyl group.

A compound of formula IIf can be deprotected to the corresponding free amine wherein R$_7$ is hydrogen by conventional methods.

It is also possible to synthesize the monomer building blocks of formula II according to Scheme II.

SCHEME II

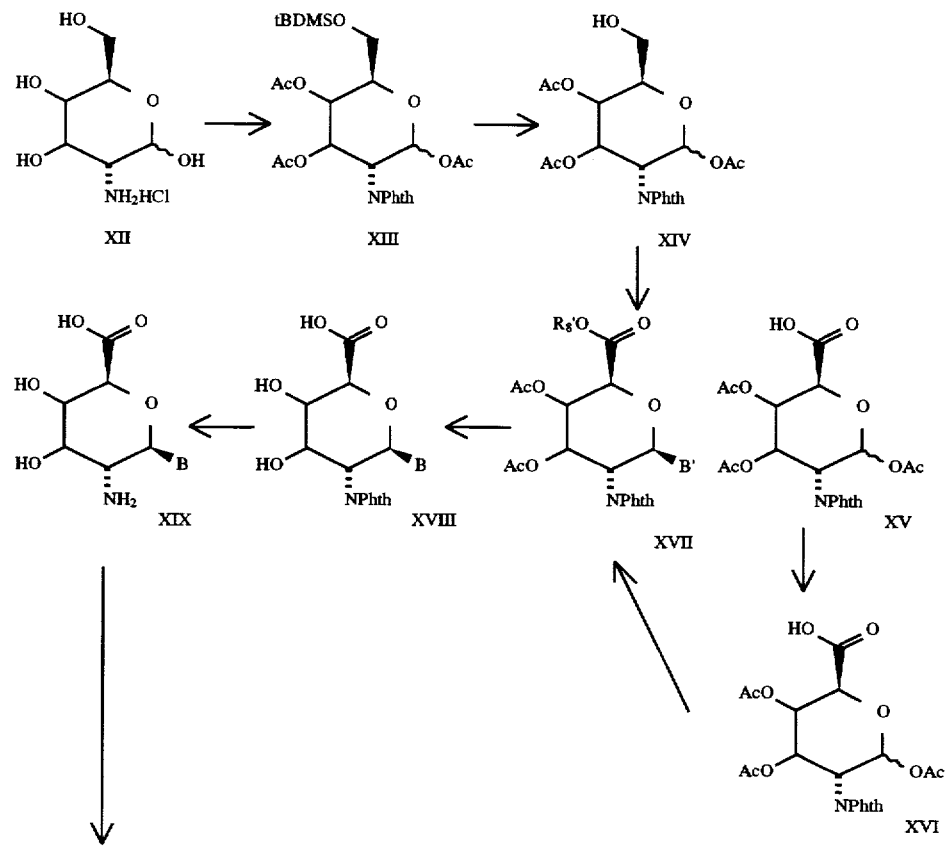

-continued
SCHEME II

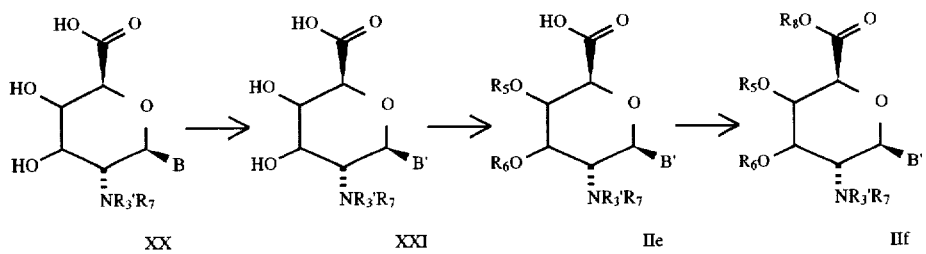

wherein Ac is acetyl, tBDMSO is tert-butyldimethylsilyl ether, Phth is phthalimide, $R_8$ is an acid protecting group, B' is a protected nucleobase, and B, $R_3'$, $R_5$, $R_6$, and $R_7$ are as described above.

As set forth in Scheme II, a compound of formula XII, a known compound or compound prepared by known methods, is converted to a corresponding compound of formula XIII, for example, by reaction with phthalic anhydride in an anhydrous solvent such as pyridine, followed by reaction with excess tert-butyldimethylsilyl chloride and subsequently reaction with acetic anhydride.

A compound of formula XIII is selectively deprotected to the corresponding compound of formula XIV by reaction with acidic catalysis in a protic solvent, preferably acid resin in $CH_3OH$. The resultant primary alcohol XIV is oxidized, preferably with ruthenium chloride catalyzed sodium periodate in a mixed solvent system of $H_2O/CH_3CN/CCl_4$. The resulting carboxylic acid is protected with a conventional acid protecting group by conventional means, such as with $CH_3I$ in DMF in the presence of $NaHCO_3$ giving compound of Formula XVI.

A compound of formula XVI is converted to the corresponding compound of formula XVII by reaction with a Lewis acid catalyst in the presence of persilylated, protected nucleobase in an anhydrous, aprotic solvent, preferably with $SnCl_4$ or trimethylsilyl trifluoromethansulfonate in $CH_3CN$ or $ClCH_2CH_2Cl$ at a temperature of 25°–80° C.

A compound of formula XVII is converted to the corresponding compound of formula XVIII by reaction with aqueous acid in a polar co-solvent, preferably HCl in tetrahydrofuran at a temperature range of 20°–50° C.

A compound of formula XVIII is converted to the corresponding compound of formula XIX by reaction with a primary amine in a polar protic solvent, preferably methylamine or hydrazine in $CH_3OH$ at temperature range of 25°–50° C.

When in formula XIX $R_3$ is hydrogen, a compound of formula XIX is converted to the corresponding compound of formula XX by reaction with N-(9-fluorenylmethoxycarbonyloxy)succinimide in a solvent such as aqueous dimethylformamide in the presence of $NaHCO_3$.

When in formula XIX $R_3$ is lower alkyl, a compound of formula XIX is converted to the corresponding compound of formula XX by reaction with 1 equivalent of an aldehyde and sodium cyanoborohydride in a polar solvent, preferably methanol, then followed by reaction with N-(9-fluorenylmethoxycarbonyloxy)succinimide in a solvent such as aqueous dimethylformamide in the presence of $NaHCO_3$.

At this point, the nucleobase B in the compound of formula XX is converted to its protected form by reaction with excess activated acyl donating group such as benzoic anhydride or acetyl chloride in a n anhydrous solvent such as 1,4-dioxane to give a compound of formula XX in which B' is a protected nucleobase.

A compound of formula XXI is converted to the corresponding compound of formula IIe by reaction with a conventional hydroxy protecting group reagent under conditions known in the art to effect selective reaction at hydroxy groups. The preferred method is by reaction with excess silylating agent, such as chlorotrialkylsilane in the presence of a base, specifically, with an excess of both triethylsilyl chloride and imidazole in a polar solvent such as dimethylformamide.

A compound of formula IIe is converted to the corresponding compound of formula IIf by conventional methods of adding an acid protecting group, preferably by reaction with benzyl bromide in presence of $NaHCO_3$ in dimethylformamide.

A compound of formula IIf can be deprotected to the corresponding free amine wherein $R_7$ is hydrogen by conventional methods.

SYNTHESIS OF OLIGOMERS

Assembly of the suitably protected monomeric building blocks into oligomers can be carried out by solid phase methodology or by conventional solution phase coupling procedures. A detailed procedure for the solid phase synthesis is illustrated in Example 6. For reference, a number of reviews on the solid phase procedure have been published including one that utilizes 9-fluorenylmethoxycarbonyl-protected amino acids (Fields, G. and Noble, R. Int. J. Peptide Protein Res. 1990, 35, 161–214). By selecting the appropriate linkers known in the art for attachment of the first residue of formula II and by application of the appropriate cleavage conditions after completion of the oligomerization process, it is possible to obtain the carboxy terminal such that Y is as described. It is also possible to chose a linker which, upon cleavage after completion of the oligomerization process on the solid phase, generates a free acid which is then modified to the appropriate carboxy substitution by conventional means.

The substitution of X is determined by the cleavage of the final amine protecting group after completion of the oligomerization process on the solid phase followed by modification of the free amine where necessary, specifically by reaction with 1 equivalent of a lower alkylaldehyde and sodium cyanoborohydride in a polar solvent, such as, methanol and/or by reaction with an acyl anhydride in polar solvent. The oligomer is cleaved and deprotected from a solid phase by application of conditions known in the art.

Deprotection of the resultant oligomer is effected in 2 steps: treatment with $NH_3$ saturated EtOH or with 30% (wt/vol) $NH_4OH$ (aqueous) at 70° C. for 12 hours. After removal of the solvent, the residue is treated with a desilylating agent, preferably tetrabutylammonium fluoride in tetrahydrofuran at room temperature for 12 hours followed by purification using a size exclusion column according to standard ribooligonucleotide purification protocols known in the literature.

The resultant product of formula I is isolated by conventional reversed phase and/or size exclusion chromatography.

Synthesis by solution phase procedure is illustrated in Scheme III and Example 5.

process followed by modification of the free amine where necessary, specifically for $R_3$ is lower alkyl, for example, by reaction with 1 equivalent of a lower alkylaldehyde and sodium cyanoborohydride in a polar solvent such as methanol and/or by reaction with an acyl anhydride in polar solvent. An oligomer of formula I is obtained by removal of the silyl or acyl hydroxy protecting groups $R_5$ and $R_6$ and by applications of the appropriate conditions to transform the $R_8'$ ester into a free acid by hydrolysis, into another ester by

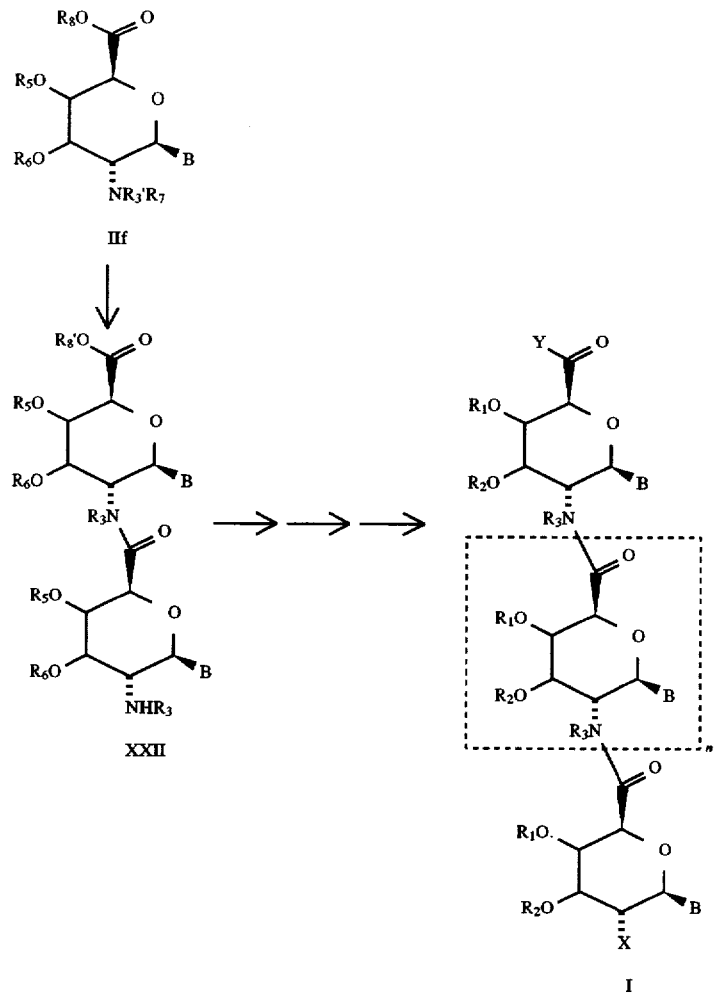

wherein $R_1$, $R_2$, $R_3$, $R_5$, $R_6$, $R_7$, $R_8$, B and X are as described above and $R_8'$ is an acid protecting group.

As set forth in Scheme III, a compound of formula IIf is deprotected at the amino terminus and the resulting compound is coupled to another moiety represented by formula II using a coupling agent, such as [O-(7-azabenzotriazol-1-yl)- 1,1,3,3-tetramethyluronium hexafluoro-phosphate]in a polar solvent such as dimethylformamide to form an oligomer of formula XXII. The resultant coupling product of formula XXII can be isolated by conventional means such as chromatographic separations, preferably by silica gel flash column chromatography.

An oligomer of formula XXII is further elongated by repetition of the procedure described for the conversion of formula IIf to an oligomer of formula XXII. The substitution of X is determined by the cleavage of the final amine protecting group after completion of the oligomerization transesterification, or into substituted or unsubstituted amine by treatment with the appropriate amine under amidation conditions. A substituted or unsubstituted carboxamide may also be obtained by coupling the free acid oligomer ($R_8$ is H) with the appropriate amine under amide bond forming conditions.

In both solution and solid phase synthesis cases, a compound of formula XXII is converted to the corresponding compound of formula I with respect to transformation of $R_5$ and $R_6$ to $R_1$ and $R_2$ according to known conventional methods.

The resultant product of formula I is isolated by conventional chromatographic means, preferably by HPLC.

The invention also relates to a pharmaceutical composition which decreases the production of a target protein in a cell, which comprises any of the above-described compounds of formula I in an amount effective to bind to the nucleic acid (for example mRNA) sequence encoding the target protein in said cell and thereby decrease production of said protein, and a pharmaceutically acceptable carrier.

The dose ranges for the administration of the antisense oligomers may be determined by those of ordinary skill in the art without undue experimentation. In general, appropriate dosages are those which are large enough to produce the desired effect. The dosage should not be so large as to cause adverse side effects, such as unwanted cross-reactions, anaphylactic reactions, and the like. Generally, the dosage will vary with the age, condition, sex and extent of disease in the patient, counter-indications, if any, immune tolerance and other such variables, to be adjusted by the individual physician. The antisense oligomers can be administered topically, for example, intradermally or as an ointment on the skin, parenterally by injection or by gradual infusion over time. They can be administered intravenously, intraperitoneally, intramuscularly, subcutaneously or orally.

Preparations for parenteral administration include sterile or aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral carriers include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. In particular, carriers capable of transporting oligomers to cells and into cells may be used, for example liposomes, PEGylated liposomes, or cationic lipids. Preservatives and other additives may also be present, such as anti-microbials, anti-oxidants, chelating agents, inert gases and the like. See, generally, *Remington's Pharmaceutical Science*, 18th Ed., Mack Eds., 1990.

The following Examples are provided to further describe the invention and are not intended to limit it in any way.

All reactions were performed under dry nitrogen atmosphere a t ambient temperature except where noted. Reagents were used without further purification except where noted. Dichloromethane ($CH_2Cl_2$), dichloroethane ($ClCH_2CH_2Cl$), and 2,6-lutidine were distilled over $CaH_2$ under dry nitrogen atmosphere. Other solvents were taken from freshly open bottle purchased from Fisher Scientific. Silica gel flash columns were run with EM Science (230–400 Mesh). Ion exchange columns were run with Biorad Ag 2X8 resin. HPLC was performed with a dual pump TSP HPLC system and integrator.

The following abbreviations are used in the description of experimental procedures: eq for equivalent; TMSOTf for trimethylsilyl trifluoro-methanesulfonate; $NH_4OH$ for ammonium hydroxide; Fmoc-O-succinimide for N-(9-fluorenylmethoxycarbonyloxy)succinimide, DMF for dimethyl-formamide, $NaHCO_3$ for sodium bicarbonate, TEMPO for 2,2,6,6-tetramethyl-1piperidinyloxy free radical, NaClO for sodium hypochlorite, $NaClO_2$ for sodium chlorite, tBDMSOTf for tert-butyldimethylsilyl trifluoromethane-sulfonate, HATU [O-(7-azabenzotriazol-1-yl)-1,1,3,3-tetramethyluronium hexafluorophosphate], DIPEA for diisopropyl-ethylamine, Knorr for p-(R, S)-α-[1-(9H-fluoren-9-yl)-methoxy-formamido]-2,4-dimethoxybenzyl]-phenoxyacetic acid, $CH_3CN$ for acetonitrile, $CH_2Cl_2$ for dichloromethane, $CH_3OH$ for methyl alcohol, $ClCH_2CH_2Cl$ for dichloroethane.

EXAMPLE 1A

Synthesis of Thymine Building Block a) To a suspension of 1.14 g (9.05 mmol) of thymine in 30 mL of dry $CH_3CN$ was added BSA (N,O-bis (trimethylsilyl)acetamide) (4.46 mL, 18.04 mmol) and this mixture was heated to 80° C. for 15 minutes resulting in a clear solution. After the solution was cooled to room temperature, 2-deoxy-2-[(trifluoroacetyl) amino]-β-D-glucopyranose-1,3,4,6-tetraacetate, (2.00 g, 4.51 mmol) was added followed by 1.74 mL (9.00 mmol) of TMSOTf (trimethylsilyltrifluoromethanesulfonate). The resulting clear solution was then stirred at room temperature for 15 minutes before heating to 85° C. for 12 h. At this time, TLC indicated the consumption of the tetraacetate. The reaction mixture was cooled and 0.756 g of $NaHCO_3$ followed by 5 mL of $H_2O$ was added. The reaction mixture was stirred for an additional hour. At this time, the suspension was diluted with addition of 50 mL each of $CH_2Cl_2$ and $H_2O$. The suspension was filtered and the solid was rinsed with $CH_2Cl_2$. The filtrate was extracted successively with saturated, aqueous $NaHCO_3$ and brine. The organic layer was dried over $MgSO_4$, filtered, and the filtrate concentrated in vacuo resulting in 2.14 g of a beige foam. This residue was recrystallized from $CH_3OH/H_2O$ yielding 1.76 g of the desired product, 1-[3,4,6-tri-O-acetyl-2-(trifluoroacetylamino)-2-deoxy-β-D-gluco-pyranosyl] thymine; the mother liquor yielded a further 0.058 g of this product. The total yield was thus 1.82 g (79%). $^1H$ NMR: (DMSO-$d_6$) δ anomeric H-1 5.88 (d, 1H), thymine —$CH_3$ 1.769 (s, 3H). Microanalysis: calculated for $C_{19}H_{22}F_3N_3O_{10}$: C 44.80, H 4.35, N 8.25; found: C 44.82, H 4.23, N 8.16. FAB-MS: m/z 510 for $(M+1))^+$.

b) To 11 g (21.61 mmol) of 1-[3,4,6-tri-O-acetyl-2-(trifluoroacetylamino)-2-deoxy- 1-D-glucopyranosyl] thymine, the thymine building block was added a solution containing 22 mL of triethylamine ($Et_3N$), 110 mL of $CH_3OH$, and 88 mL of $H_2O$ forming a clear and colorless solution. After 4 hours, when TLC indicated the completion of the reaction, the solution was concentrated in vacuo. Additional $CH_3OH$ was added and the solution was evaporated again to a beige foam. The residue was recrystallized from $H_2O$ yielding 5.97 g (72%) of the expected triol. $^1H$ NMR: (DMSO-$d_6$): δ anomeric H-1 5.57 (d, 1H), thymine —$CH_3$ 1.78 (s, 3H). FAB-MS: m/z 384 for $(M+1)^+$.

To 4.37 g (11.44 mmol) of the triol obtained as described above was added 80 mL of a solution containing 20 mL of 30% (wt/vol) $NH_4OH$ and 60 mL of $H_2O$. The resulting solution was stirred for 12 h at room before thorough evaporation to a light brown solid: 1-(2-amino-2-deoxy-β-D-glucopyranosyl)thymine, 4.84 g (crude yield >100%). $^1H$ NMR: ($D_2O$):δ anomeric H-1 5.69 (d, 1H), thymine —$CH_3$ 1.91 (s, 3H). FAB-MS: m/z 288 for $(M+1)^+$.

c) To 4.87 g (16.97 mmol) of 1-(2-amino-2-deoxy-β-D-glucopyranosyl)thymine, amino sugar was added 48 mL of $H_2O$ and 127 mL of 1,4-dioxane. To this solution was added N-(9-fluorenylmethoxy-carbonyloxy)succinimide (10.22 g, 30.91 mmol) as a solution in 60 mL of 1,4-dioxane. This was followed by addition of 1.15 g (13.67 mmol) of $NaHCO_3$. This turbid solution was stirred for 12 h at room temperature. At this time when TLC indicated the consumption of the amino sugar, the reaction mixture was concentrated to dryness in vacuo. To the residue was added 200 mL of $H_2O$ and 700 mL of ethyl ether ($Et_2$). This 2 phase suspension was stirred for 24 h at room temperature before filtration and rinsing of the resultant solid with $H_2O$ and $Et_2O$. The solid was dried under vacuum, then suspended in $Et_2O$ again. Filtration and drying of the solid resulted in 3.84 g (66%) of the N-Fmoc protected amino sugar, 1-[2-deoxy-2- [[(9H-fluoren-9-ylmethoxy)carbonyl]amino]-β-D-glucopyranosyl]-thymine. $^1H$ NMR: (DMSO-$d_6$): δ anomeric H-1 5.49 (d, 1H), Fmoc methine 4.59 (m, 1H), thymine —$CH_3$ 1.75 (s, 3H). FAB-MS: m/z 510 for $(M+1)^+$.

d) To a 20 mL dry CH$_2$Cl$_2$ suspension of 2.0 g (3.94 mmol) of 1-|2-deoxy-2- ||9H-fluoren-9-ylmethoxy)carbonyl|amino|-β-D-glucopyranosyl|thymine was added 8.25 mL (70.42 mmol) of 2.6-lutidine. The resulting solution was cooled to ≈3° C. with stirring under nitrogen atmosphere before addition of 4.07 mL (17.7 mmol) of tert-butyldimethylsilyl trifluoromethanesulfonate. After 30 minutes, another 4.07 mL of tert-butyldimethylsilyl trifluoromethanesulfonate was added. The reaction mixture was brought to room temperature after 30 minutes and the reaction was stirred in this manner overnight. At this time, the reaction was worked up by dilution with 100 mL of CH$_2$Cl$_2$ and this solution was extracted once with 50 mL of 1N HCl aq., followed by extraction twice with H$_2$O. The combined aqueous layers were extracted once with CH$_2$Cl$_2$. The combined CH$_2$Cl$_2$ layers were washed twice with saturated, aqueous NaHCO$_3$, once with brine, dried with MgSO$_4$, filtered, and concentrated in vacuo. The residue was chromatographed on silica eluted sequentially with CHCl$_3$ and 1% CH$_3$OH/CHCl$_3$. This yielded the desired 1-|2-deoxy-2-||(9H-fluoren-9-ylmethoxy)carbonyl|amino|-|3,4,5-tris-O- |(1,1 -dimethyl-ethyl)dimethylsilyl|-β-D-glucopyranosyl|thymine as a white foam (2.56 g, 76%). $^1$H NMR: (DMSO-d 6): δ thymine H-6 7.55 (s, 1H), anomeric H-1 5.64 (d, 1H), Fmoc methine 4.37 (m, 1H), thymine —CH$_3$ 1.74 (s, 3H). FAB-MS: m/z 852 for (M+1)$^+$.

e) To a 3° C. solution of 5.6 mL of distilled CH$_2$Cl$_2$ and 5.6 mL of CH$_3$OH containing 1.14 g (1.34 mmol) 1 - |2-deoxy-2- ||(9H-fluoren-9-ylmethoxy)carbonyl|amino|-|3,4,6-tris-O- |(1,1 -dimethylethyl)dimethyl-silyl|-β-D-glucopyranosyl|thymine was added 0.53 g (2.28 mmol) of CSA (dl-10-camphorsulfonic acid). The resulting solution was stirred under nitrogen atmosphere and the temperature was maintained a t approximately 3° C. for 120 minutes. The reaction was terminated by addition of saturated, aqueous NaHCO$_3$, followed by dilution with 50 mL of CH$_2$Cl$_2$. The resulting solution was extracted twice with saturated, aqueous NaHCO$_3$ and once with H$_2$O. The combined aqueous layers were extracted once with CH$_2$Cl$_2$. The combined CH$_2$Cl$_2$ layers were washed once with brine, dried with MgSO$_4$, filtered, and concentrated in vacuo. The residue was chromatographed on silica eluted sequentially with 1% to 2% CH$_3$OH/CHCl$_3$. This yielded, 1- |2-deoxy-2- ||(9H-fluoren-9-ylmethoxy)carbonyl|amino|- |3,4-bis-O- |(1,1-dimethylethyl) dimethylsilyl|-β-D-glucopyranosyl|thymine as a white foam (0.84 g, 85%). Microanalysis: calculated for C$_{38}$H$_{55}$N$_3$O$_8$Si$_2$—H$_2$O C 61.84, H 7.51, N 5.69; found: C 61.56, H 7.28, N 5.48.

f) To 0.82 g (0.1.11 mmol) of 1-|2-deoxy-2-||(9H-fluoren-9-ylmethoxy)carbonyl|amino|-|3,4-bis-O-|(1,1-dimethylethyl)dimethylsilyl|) β-D-glucopyranosyl|thymine in 33 mL of distilled CH$_2$Cl$_2$ was added 0.039 g (0.33 mmol) of KBr and 0.019 g (0.056 mmol) of (n-Bu)$_4$NHSO$_4$. This suspension was cooled to 3° C. with stirring under nitrogen atmosphere. To the cooled suspension was added 0.0088 g (0.056 mmol) of TEMPO (2,2,6,6-tetramethyl-1-piperidinyloxy free radical). To this mixture was added a solution containing 1.33 mL of 1.0M (aq) NaClO, 1.33 mL of saturated NaHCO$_3$, and 1.33 mL of saturated NaCl. The reaction was stirred for 30 minutes. At this time, another solution containing 1.33 mL of 1.0M (aq) NaClO, 1.33 mL of saturated NaHCO$_3$, and 1.33 mL of saturated NaCl was added. This caused the formation of a bright yellow color. At this point, the reaction was terminated by dilution with CH$_2$Cl$_2$ (50 mL) and the aqueous layer was separated. The organic layer was concentrated in vacuo.

The resulting opaque residue was dissolved in 10 mL of tert-butyl alcohol and 10 mL of H$_2$O. To this stirred solution was added 1.53 g (11.10 mmol) of NaH$_2$PO$_4$ and 4.70 mL (44.40 mmol) of 2-methyl-2-butene. To this solution was added 0.80 g (8.88 mmol) of NaClO$_2$. This mixture was stirred at room temperature for 30 minutes. At this time, the reaction mixture was poured into a mixture of EtOAc (100 mL) and H$_2$O (10 mL) acidified to pH=2 with 10% (wt/vol) aqueous citric acid. The layers were separated and the organic layer was twice extracted with H$_2$O. The aqueous layers were back extracted once with EtOAc. The organic layers were combined, washed with brine, dried with MgSO$_4$, filtered and concentrated in vacuo to a white foam residue. The desired carboxylic acid product, 1,2-dideoxy-1-|1,2-dihydro-5-methyl|-2,4-dioxo- 1-pyrimidinyl)- ||(9H-fluoren-9-ylmethoxy)carbonyl|amino|-|3,4-bis-O- |(1,1-dimethylethyl)dimethylsilyl|-β-D-glucopyranuronic acid was obtained by chromatography of the residue from a silica gel flash column eluted with 4 to 10% CH$_3$OH/CHCl$_3$ in 62% yield (0.51 g). $^1$H NMR: (DMSO-d$_6$): δ anomeric H-1 5.92 (d, 1H), Fmoc methine 4.28 (m, 1H), thymine —CH$_3$ 1.77 (s, 3H), 0.91 tert-butyl (s, 9H), 0.77 ppm tert-butyl (s, 9H). FAB-HRMS: calculated for (M+1)$^+$: 752.3398; found for (M+1)$^+$: 752.3397.

EXAMPLE 1B

Synthesis of Thymine Building Block

Steps a)–c) were performed as set forth in Example 1A.

d) To a 5 mL dry DMF solution of 0.751 g (1.50 mmol) of 1-|2-deoxy-2-|[9H-fluoren-9-ylmethoxy)carbonyl| amino|-β-D-glucopyranosyl|thymine was added 1.60 g (23.6 mmol) of imidazole and a catalytic quantity (≈1 mg) of DMAP (para-N,N-dimethylaminopyridine). The resulting solution was cooled to ≈2° C. with stirring under nitrogen atmosphere before addition of 0.93 mL (5.9 mmol) of chloroisopropyl-dimethylsilane. The reaction mixture was brought to room temperature after 5 minutes. After 90 minutes, another portion (0.93 mL, 5.9 mmol) of chloroisopropyldimethylsilane was added. After 30 minutes, TLC indicated the conversion of starting material to a single product. The reaction was terminated by dilution with 50 mL of EtOAc (ethyl acetate) and this solution was extracted twice with H$_2$O, followed by extraction with 10% (wt/vol) aqueous citric acid. The organic layer was extracted once again with H$_2$O. The combined aqueous layers were extracted once with EtOAc. The combined EtOAc layers were washed once with brine, dried with MgSO$_4$, filtered, and concentrated in vacuo. The residue was chromatographed on silica eluted sequentially with CHCl$_3$ and 1% CH$_3$OH/CHCl$_3$. This yielded the desired 1-|2-deoxy-2-|[9H-fluoren-9-ylmethoxy)carbonyl]amino|- |3,4,5-tris-O-[(1-methylethyl)dimethylsilyl|-β-D-glucopyranosyl|thymine as a white foam (1.01 g, 83%). $^1$H NMR: (CDCl$_3$): δ anomeric H-1 5.62 (d, 1H), Fmoc methine 4.29 (m, 1H), thymine —CH$_3$ 1.91 (s, 3H). FAB-MS: m/z 810 for (M+1)$^+$. Microanalysis: calculated for C$_{41}$, H$_{63}$N$_3$O$_8$Si$_3$: C 60.78, H 7.84, N 5.19; found: C 60.75, H 7.82, N 5.27.

e) To a –30° C. solution of 5 mL of distilled CH$_2$Cl$_2$ and 1.2 mL of CH$_3$OH containing 0.25 g (0.31 mmol) of N-Fmoc protected amino sugar 1-|2-deoxy-2-||9H-fluoren-9-ylmethoxy)carbonyl|amino|-|3,4,6-tris-O-|(1-methylethyl)dimethylsilyl|-β-D-glucopyranosyl|thymine was added 0.014 g (0.062 mmol) of CSA (dl-10-camphorsulfonic acid). The resulting solution was stirred under nitrogen atmosphere and the temperature was maintained at approximately –30° C. for 105 minutes. The reaction was terminated by addition of saturated NaHCO$_3$, followed by dilution with 50 mL of EtOAc. The resulting solution was extracted twice with saturated, aqueous NaHCO$_3$ and once with H$_2$O. The combined aqueous layers were extracted once with EtOAc. The combined EtOAc layers were washed once with brine, dried with MgSO$_4$, filtered, and concentrated in vacuo. The residue was chromatographed on silica eluted sequentially with CHCl$_3$ and then 1% to 2% CH$_3$OH/CHCl$_3$. This yielded 1-|2-deoxy-2-||9H-fluoren-9-ylmethoxy)carbonyl|amino|- |3,4-bis-O-|(1-methylethyl)dimethylsilyl|-β-D-glucopyranosyl| thymine as a white foam (0.196 g, 89%). $^1$H NMR: (DMSO-d$_6$): δ anomeric H-1 5.62 (d, 1H), Fmoc methine 4.36 (m, 1H), thymine —CH$_3$ 1.76 (s, 3H), 1.75–1.96 silylisopropyl (m, 14H), −0.03 0.00 ppm silylmethyl (4 singlets, 12H). FAB-MS: (m/z 910 for (M+1)$^+$.

f) To 0.18 g (0.25 mmol) of 1-|2-deoxy-2-||9H-fluoren-9-ylmethoxy) carbonyl|amino|- |3,4-bis-O- |(1-methylethyl)dimethylsilyl|-β-D-glucopyranosyl|thymine in 10 mL of distilled CH$_2$Cl$_2$ was added 0.0030 g (0.025 mmol) of KBr and 0.0043 g (0.013 mmol) of (n-Bu)$_4$NHSO$_4$. This suspension was cooled to −6° C. with stirring under nitrogen atmosphere. To the cooled suspension was added 0.0004 g (0.0025 mmol) of TEMPO (2,2,6,6-tetramethyl-1-piperidinyloxy free radical). To this mixture was added in 3 portions separated by 10 minutes a solution containing 0.33 mL of 1.24 M NaClO, 0.33 mL saturated NaHCO$_3$, and 0.33 mL saturated NaCl. The temperature was raised to 0° C. and the reaction was stirred for 30 minutes. At this point, the reaction was terminated by dilution with EtOAc (50 mL) and the organic solution was twice extracted with H$_2$O. The aqueous layers were extracted once with EtOAc. The organic layers were combined, washed with brine, dried with MgSO$_4$, filtered and concentrated in vacuo.

The resulting opaque residue was dissolved in 3 mL of tert-butyl alcohol and 3 mL of H$_2$O. To this stirred solution was added 0.28 g (2.03 mmol) of NaH$_2$PO$_4$ and 1.08 mL (10.16 mmol) of 2-methyl-2-butene. To this solution was added 0.23 g (2.54 mmol) of NaClO$_2$. This mixture was stirred at room temperature for 30 min. At this time, the reaction mixture was poured into a mixture of EtOAc (50 mL) and H$_2$O acidified to pH=2 with 10% (wt/vol) aqueous citric acid. The layers were separated and the organic layer was twice extracted with H$_2$O. The organic layers were combined, washed with brine, dried with MgSO$_4$, filtered and concentrated in vacuo to a white foam residue. The desired carboxylic acid product, 1,2-dideoxy-1-|1,2-dihydro-5-methyl|-2,4-dioxo-1-pyrimidinyl)-||(9H-fluoren-9-ylmethoxy)carbonyl|amino|-|3,4-bis-O- |(1-methylethyl)dimethylsilyl||-β-D-glucopyranuronic acid was obtained by chromatography of the residue from a silica gel flash column eluted with 5 to 20% CH$_3$OH/CHCl$_3$ in 74% yield (0.136 g). $^1$H NMR: (DMSO-d$_6$): δ anomeric H-1 5.55 (d, 1H), Fmoc methine 4.36 (m, 1H), thymine —CH$_3$ 1.75 (s, 3H), 1.75–1.96 silylisopropyl (m, 14H), −0.03 to 0.00 ppm silylmethyl (m, 12H). FAB-MS: 724 for (M+1)$^+$. Microanalysis: calculated for C$_{36}$H$_{49}$N$_3$O$_9$Si$_2$—H$_2$O C 58.99, H 6.88, N 5.73; found: C 58.82, H 6.54, N586.

EXAMPLE 2

Synthesis of Cytosine Building Block a) To a suspension of N-benzoylcytosine (29.11 g, 135.40 mmol) in 250 mL of distilled ClCH$_2$CH$_2$Cl was added 66.80 ml (270.82 mmol) of BSA. This suspension was heated to a gentle reflux for 40 min during which time a clear solution was effected. At this time, the solution was cooled to room temperature and 20 g (45.15 mmol) of 2-deoxy-2-|(trifluoroacetyl)amino|-β-D-glucopyranose-1,3,4,6-tetraacetate was add followed by a solution of 100 mL of ClCH$_2$CH$_2$Cl containing freshly distilled SnCl$_4$ (15.17 mL, 135.42 mmol). This resulting slightly yellow solution was refluxed for 2 h. At this time, the reaction was cooled to room temperature and 57 g of NaHCO$_3$ was added and stirred before the addition of 22 mL of H$_2$O. The mixture was stirred for an additional 20 min at room temperature. The suspension was filtered and washed through a pad of celite with CHCl$_3$. The filtrate was washed with saturated, aqueous NaHCO$_3$ and brine. The organic layer was further treated with charcoal before filtration through a pad of celite. The filtrate was dried over Na$_2$SO$_4$, filtered and concentrated in vacuo to a yellowish foam. This residue was chromatographed on silica gel eluted with CH$_2$Cl$_2$ and 1 to 3.5% CH$_3$OH/CH$_2$Cl$_2$. The product was further purified by recrystallization from CH$_3$OH/H$_2$O. As a single crop of white crystals the desired glycosylation product, N- |1,2-dihydro-2-oxo- 1-|3,4,6-tri-O-acetyl-2-deoxy-2-|(trifluoroacetyl)amino|-β-D-glucopyranosyl||-4-pyrimidinyl|benzamide was obtained (9.22 g, 34%). $^1$H NMR: (CDCl$_3$): δ anomeric H-1 6.21 (d, 1H), acetyl ester 2.06 (s, 3H), acetyl ester 1.82 (s, 3H). FAB-MS: m/z 599 for (M+1)$^+$, 1197 for (2M+1)$^+$. Microanalysis: calculated for C$_{25}$H$_{25}$N$_4$O$_{10}$C 50.17, H 4.21, N 9.36; found: C 50.01, H 4.00, N 9.16.

b) 19 g (31.77 mmol) of N-|1,2-dihydro-2-oxo-1-|3,4,6-tri-O-acetyl-2-deoxy-2- |(trifluoroacetyl)amino|-β-D-glucopyranosyl||-4-pyrimidinyl|-benzamide was treated with a solution of 57 mL of Et$_3$N, 285 mL of CH$_3$OH, and 228 mL of H$_2$O. This solution was stirred at room temperature for 4.5 h. At this time, the solution was concentrated to dryness in vacuo. The residue was treated with 60 mL of 30% (wt/vol) NH$_4$OH diluted with 140 mL of H$_2$O for 12 h at room temperature. The reaction mixture was then concentrated to dryness in vacuo. The residue was dissolved in 50 mL of H$_2$O and loaded to an ion exchange column containing 400 mL of Ag 2×8, HO— form and eluted with H$_2$O. The appropriate fractions according to TLC were combined, frozen, and lyophilized to a white powder. The free amino sugar, 1-(2-amino-2-deoxy-β-D-glucopyranosyl) cytosine was obtained in 96% yield (8.30 g). $^1$H NMR: (D$_2$O): δ cytosine-H$_{6\,7.71}$ (d, 1H), cytosine-H$_{5\,6.10}$ (d, 1H), anomeric H-1 5.64 (d, 1H). CSI-MS: m/z 273 for (M+1)+, 545 for (2M+1)$^+$. Microanalysis: calculated for C$_{10}$H$_{16}$N$_4$O$_5$ C 44.12, H 5.92, N 20.81; found: C 44.02, H 5.94, N 20.81.

c) To 0.80 g (2.94 mmol) of 1-(2'-amino-2'-deoxy-β-D-gluco-pyranosyl)cytosine was added 4 mL of H$_2$O. To this solution was added a 20 mL solution of 1,4-dioxane containing 1.19 g (3.53 mmol) N-(9-fluorenylmethoxycarbonyloxy)succinimide and an additional volume of 1,4-dioxane (12 mL) was added. Sodium bicarbonate (0.15 g, 1.79 mmol) was added as an 8 mL H$_2$O solution to the reaction mixture. This mixture was stirred at room temperature for 12 h. At this time TLC indicated the consumption of starting material and the reaction solvents were removed in vacuo leaving a white gum. This residue was treated with 20 mL of H$_2$O and excess ether (200 mL). The suspension was stirred for several hours, filtered and resuspended in CH$_2$Cl$_2$, Et$_2$O and H$_2$O for 12 h. The suspension was filtered and the solid dried under vacuum yielding 1.00 g (57%) of 1-|2-deoxy-2- ||(9H-fluoren-9-ylmethoxy)carbonyl|amino|-β-D-glucopyranosyl|cytosine. $^1$H NMR: (DMSO-d$_6$): δ cytosine-H$_{6\,7.50}$ (d, 1H), cytosine-H$_{5\,6.67}$ (d, 1H), anomeric H-1 5.66 (d, 1H). CSI-MS: m/z 495 for (M+1)$^+$. Microanalysis: calculated for C$_{25}$H$_{26}$N$_4$O$_7$ C 60.98, H 5.82, N 10.61; found: C 61.10, H 5.63, N10.50.

d) To 15. 50 g (31.38 mmol) of 1-|2-deoxy-2-||(9H-fluoren-9-ylmethoxy)carbonyl|amino|-β-D- glucopyranosyl|cytosine was added 1.2 liters of 200 proof ethanol and this solution was heated to reflux. At reflux, 7.09 g (31.37 mmol) of benzoic anhydride was added. Every hour for 4 hours, an additional portion of 7.09 g of benzoic anhydride was added to the refluxing solution. After a total of 5 hours reaction time, TLC indicated the consumption of the starting material. At this time the reaction mixture was concentrated to near dryness in vacuo and 500 mL of $Et_2O$ was added; this suspension was filtered and rinsed with $Et_2O$. The resulting solid was recrystallized from $CHCl_3$, giving 7.48 g (40%) of N-|1-|2-deoxy-2-||(9H-fluoren-9-ylmethoxy)carbonyl|amino|-β-D-glucopyranosyl|-1,2-dihydro-2-oxo-4-pyrimidinyl|benzamide. $^1$H NMR: (DMSO-$d_6$): δ anomeric H-1 5.75 (m, 1H). CSI-MS: m/z 599 for $(M+1)^+$ and 621 for $(M+Na)^+$.

e) To 0.250 g (0.42 mmol) of N-|1,2-dihydro-2-oxo-1-(2-deoxy-2-||(9H-fluoren-9-ylmethoxy)carbonyl|amino|-β-D-glucopyranosyl)-4-pyrimidinyl|benzamide was added 3 mL of distilled $CH_2Cl_2$ and 0.876 mL (7.52 mmol) of distilled 2,6-lutidine. To this white suspension cooled to 0° C. was added 0.43 mL (1.88 mmol) of tBDMSOTf (tert-butyldimethylsilyl trifluoromethanesulfonate). Stirring was continued at 0° C. for 5 minutes before the cold bath was removed and the reaction was allowed to stir at room temperature. After 90 minutes, an additional portion of tBDMSOTf (0.43 mL) was added. The reaction was stirred at room temperature for 4 h. At this time, the reaction mixture was poured into EtOAc and twice extracted with $H_2O$, once with 5% (wt/vol) citric acid, once with saturated, aqueous $NaHCO_3$, and finally once with brine. The organic layer was dried with $MgSO_4$, filtered, and concentrated in vacuo to a slight white solid. This solid was loaded to a silica gel flash column and the desired silylated Product, N-|1-|2-deoxy-2-||(9H-fluoren-9-ylmethoxy)carbonyl|amino|-|3,4,6-tris-O- |(1,1-dimethylethyl)dimethylsilyl|-β-D-glucopyranosyl|- 1,2-dihydro-2-oxo-4-pyrimidinyl|benzamide was obtained by elution of the column with $CHCl_3$ and 1% $CH_3OH/CHCl_3$: 0 276 g (70%). $^1$H NMR: ($CDCl_3$): δ cytosine-$H_6$, $H_{5\;6.89}$ (br, 2H), anomeric H-1 6.12 (d, 1H). FAB-MS: m/z 941 for $(M+1)^+$. FT-IR (KBr pellet): Si —$CH_3$ 837 cm$^{-1}$.

f) To 0.46 g (0.50 mmol) of N-|1-|2-deoxy-2-|[(9H-fluoren-9-ylmethoxy)carbonyl|amino|- |3,4,6-tris-O- |(1,1-dimethylethyl) dimethylsilyl|-β-D-glucopyranosyl|-1,2-dihydro-2-oxo-4-pyrimidinyl|benzamide was added 2.0 mL of distilled $CH_2Cl_2$ and 2.0 mL of $CH_3OH$. This clear solution was cooled to 0° C. before the addition of 0.20 g (0.84 mmol) of CSA. The reaction was stirred at 0° C. for 2 h before quenching the reaction with saturated aqueous $NaHCO_3$ and dilution of the mixture with $CH_2Cl_2$. The organic layer was twice extracted with saturated, aqueous $NaHCO_3$; the combined aqueous layers are extracted once with $CH_2Cl_2$. The combined organic layers are washed with brine, dried over $MgSO_4$, filtered and the filtrate was concentrated in vacuo to a white foam. The desired primary alcohol, N-|1- |2-deoxy-2-|(trifluoroacetyl)amino|- |3,4-bis-O- |(1,1-dimethylethyl)dimethylsilyl|-[β-D-glucopyranosyl|- 1,2-dihydro-2-oxo-4-pyrimidinyl| benzamide was obtained by elution of the crude foam from a silica gel flash column eluted with $CHCl_3$ and 1 to 2% $CH_3OH/CHCl_3$: 0.31 g (74%). $^1$H NMR: ($CDCl_3$): δ anomeric H-1 6.12 (d, 1H), NH 5.30 (br d, 1H), t-butylSi 0.96 (s, 9H), t-butylSi 0.91 (s, 9H), $(CH_3)_2$Si 0.19 (s, 6H), $(CH_3)_2$Si 0.16 (s, 6H). FAB-MS: m/z 827 for $(M+1)^+$. FT-IR (KBr pellet): Si —$CH_3$ 839 cm$^{-1}$.

g) To 0.31 g (0.371 mmol) of N-|1-|2-deoxy-2-||(9H-fluoren-9-ylmethoxy)carbonyl|amino|-|3,4-bis-O-|(1,1-dimethylethyl)dimethylsilyl|-β-D-glucopyranosyl|-1,2-dihydro-2-oxo-4-pyrimidinyl|benzamide was added 0.0052 g (0.037 mmol) of KBr, 0.0063 g (0.019 mmol) of (n-Bu)$_4NHSO_4$, and 10 mL of distilled $CH_2Cl_2$. The reaction mixture was cooled to −4° C. with stirring and 0.0006 g (0.0037 mmol) of TEMPO was added. To this mixture was added in 3 portions separated by 10 min a solution containing 0.48 mL of 1.24M NaClO, 0.48 mL saturated $NaHCO_3$, and 0.48 mL saturated NaCl. The temperature was raised to 0° C. and the reaction was stirred for 1 h. At this point, the reaction was terminated by dilution with $CH_2Cl_2$ (50 mL) and the organic solution was twice extracted with $H_2O$. The aqueous layers were extracted once with $CH_2Cl_2$. The combined organic layers were washed with brine, dried with $MgSO_4$, filtered and concentrated in vacuo.

The resulting opaque residue was dissolved in 4 mL of tert-butyl alcohol and 4 mL of $H_2O$. To this stirred solution was added 0.41 g (3.00 mmol) of $NaH_2PO_4$ and 1.57 mL (14.84 mmol) of 2-methyl-2-butene. To this solution was added 0.34 g (3.71 mmol) of $NaClO_2$. This mixture was stirred at room temperature for 30 min. At this time, the reaction mixture was poured into a mixture of EtOAc (50 mL) and $H_2O$ acidified to pH=2 with 10% (wt/vol) aqueous citric acid. The layers were separated and the organic layer was twice extracted with $H_2O$. The combined organic layers were combined, washed with brine, dried with $MgSO_4$, filtered and concentrated in vacuo to a white foam residue. The desired carboxylic acid product, 1,2-dideoxy-1- |1,2-dihydro-2-oxo-4-|(phenylcarbonyl)amino|-1-pyrimidinyl|-|3,4-bis-O- |(1,1-dimethylethyl)dimethylsilyl|-2||(9H-fluoren-9-ylmethoxy)carbonyl|amino|-β-D-glucopyranuronic acid was obtained by chromatography of the residue from a silica gel flash column eluted with $CHCl_3$ and 1 to 10% $CH_3OH/CHCl_3$ in 93% yield (0.29 g). $^1$H NMR: ($CDCl_3$): anomeric H-1 6.75 (br, 1H), t-butylSi 0.98 (s, 9H), t-butylSi 0.87 (s, 9H), $(CH_3)$Si 0.22 (s, 3H), $(CH_3)$Si 0.19 (s, 3H), $(CH_3)$Si 0.10 (s, 3H), $(CH_3)$Si 0.0(s, 3H). FAB-MS: m/z 841 for $(M+1)^+$. Microanalysis: calculated for $C_{44}H_{56}N_4O_9Si_2$—$H_2O$ C 62.17, H 6.76, N 6.59; found: C 62.33, H 5.83, N 6.18.

EXAMPLE 3

Synthesis of Adenine Building Block a) In 25 mL of dry $CH_3CN$ was suspended 0.54 g (2.26 mmol) 6-N-benzoyladenine, and N,N-dibenzoyladenine and to this suspension was added 0.50 mL (4.51 mmol) of freshly distilled $SnCl_4$. An immediate solution was achieved at room temperature. To this solution was added 0.50 g (1.13 mmol) of 2-deoxy-2-|(trifluoroacetyl)amino|-β-D-glucopyranose-1,3,4,6-tetraacetate and the reaction mixture was heated for 12 h at 40° C. at which time TLC indicated the complete consumption of starting material. The reaction was cooled to room temperature and 1.89 g (22.5 mmol) of $NaHCO_3$ was added followed by the addition of 0.71 mL (39.44 mmol) of $H_2O$. This mixture was stirred at room temperature for 30 min and then filtered and washed through a pad of celite with $CH_3CN$. The filtrate was concentrated to dryness in vacuo and the residue was dissolved in EtOAC. This solution was washed with saturated, aqueous $NaHCO_3$ and brine, dried over $NaSO_4$, and filtered. The filtrate was concentrated in vacuo leaving a white foam. This foam was chromatographed on silica with 5 to 10% $CH_3OH/CH_2Cl_2$ yielding 0.46 g (66%) of the desired product, N-|9-|3,4,6-tri-O-acetyl-2-deoxy-2-|(trifluoroacetyl)amino)-β-D-glucopyranosyl)-9H-purin-6-yl|-benzamide. $^1$H NMR: ($CDCl_3$): adenine aromatic 8.38 (s, 1H), adenine aromatic 8.25 (s, 1H), anomeric H-1 6.25 (d, 1H). FAB-MS: m/z 623 for (M+1)$^+$. Microanalysis: calculated for $C_{26}H_{25}N_6O_9$—$H_2O$ C 48.75, H 4.24, N 13.12; found: C 48.84, H 4.13, N 12.88.

b) 6.59 g (10.50 mmol) of N-|9-|3,4,6-tri-O-acetyl-2-deoxy-2-|(trifluoroacetyl)amino|-β-D-glucopyranosyl|-9H-purin-6-yl|benzamide was treated with a solution of 20 mL of $Et_3N$, 100 mL of $CH_3OH$, and 80 mL of $H_2O$. This solution was stirred at room temperature for 12 h. At this time, the solution was concentrated to dryness in vacuo. The residue was treated with 160 mL of 30% (wt/vol) $NH_4OH$ for 72 h at room temperature. The reaction mixture was then concentrated to dryness in vacuo. The residue was dissolved in 50 mL of $H_2O$ and loaded to an ion exchange column containing 265 mL of Ag 2×8, HO— form and eluted with $H_2O$. The appropriate fractions according to TLC were combined, frozen, and lyophilized to a white powder. The amino sugar 9-(2-amino-2-deoxy-β-D-glucopyranosyl) adenine was obtained in 63% yield (1.98 g). $^1$H NMR: ($D_2O$): δ adenine aromatic 8.34 (s, 1H), adenine aromatic 8.21 (s, 1H), anomeric H-1 5.60 (d, 1H). FAB-MS: m/z 297 for (M+1)$^+$.

c) To 0.69 g (2.33 mmol) of 9-(2-amino-2-deoxy-β-D-glucopyranosyl)adenine was added 3.45 mL of $H_2O$. To this solution was added a 28 mL 1,4-dioxane solution of 0.94 g (2.80 mmol) of N-(9-fluorenylmethoxycarbonyloxy) succinimide. This resulted in a cloudy mixture. To this system was added 0.13 g (1.50 mmol) of $NaHCO_3$. This mixture was stirred for 12 h at room temperature. At this time, TLC indicated the consumption of starting material and the mixture was concentrated in vacuo to a dry residue. This residue was stirred for 18 h in 250 mL of $Et_2O$ and 250 ml of $H_2O$. The suspension was then filtered and the solid dried in a vacuum oven for 2 days. Thus was obtained 1.0 g (82%) of the desired 9-[2-deoxy-2-[[(9H-fluoren-9-ylmethoxy)carbonyl]-amino]-β-D-glucopyranosyl]adenine $^1$H NMR: (DMSO-$d_6$): adenine aromatic 8.19 (s, 1H), adenine aromatic 8.17 (s, 1H), anomeric H-1 6.60 (d, 1H), Fmoc-methine 4.17 (m, 1H). FAB-MS: m/z 519 for (M+1)$^+$.

d) Azeotropic evaporation of 0.50 g (0.97 mmol) of 9-[2-deoxy-2-[[(9H-fluoren-9-ylmethoxy)carbonyl]amino]-β-D-glucopyranosyl]adenine in dry pyridine was repeated three times before dissolving the residue in 20 mL of dry pyridine. To this solution was added 0.74 mL (5.79 mmol) of chlorotrimethylsilane. This reaction mixture was stirred at room temperature for 30 min. At this time, 0.56 mL (4.82 mmol) of benzoyl chloride was added and the resultant solution was stirred at room temperature for 2.5 h at which time TLC indicated the complete conversion of the starting material into product. The reaction mixture was quenched by addition of 10 mL of $H_2O$, stirred for 1.5 h, and then 40 mL of cold saturated $NaHCO_3$ was added. This 2 phase system was stirred for a n additional 3 h at which time the mixture was extracted twice with EtOAc. The EtOAc layer was washed with brine and dried over $MgSO_4$, filtered and concentrated to dryness in vacuo. The residue was dissolved in EtOAc and this solution was washed thrice with 2N HCl, thrice with saturated, aqueous $NaHCO_3$, once with brine and dried with $MgSO_4$, and filtered. The filtrate was evaporated to dryness. The residue was recrystallized from $CHCl_3$ yielding 0.48 g (64%) of the desired N-|2-deoxy-2-|[(9H-fluoren-9-ylmethoxy)carbonyl amino|-β-D-glucopyranosyl| -9H-purin-6-yl|-dibenzamide. $^1$H NMR: (DMSO-$d_6$): adenine aromatic 8.76 (s, 1H), adenine aromatic 8.67 (s, 1H), anomeric H-1 6.70 (d, 1H), Fmoc-methine 4.07 (m,1H). FAB-MS: m/z 727 for (M+1)$^+$, 749 for (M+Na)$^+$. FT-IR (KBr): amide resonance 1700 cm$^{-1}$.

e) To 0.050 g (0.069 mmol) of N-|2-deoxy-2-||(9H-fluoren-9-ylmethoxy)carbonyl|amino|-β-D-glucopyranosyl|-9H-purin-6-yl|-dibenzamide was added 2 mL of distilled $CH_2Cl_2$. To this suspension was added 0.16 mL (1.38 mmol) of 2,6-lutidine followed by 0.16 mL (0.69 mmol) of tBDMSOTf. This solution was stirred for 72 h. At this time, the reaction mixture was diluted with $CHCl_3$ and washed once with $H_2O$, twice with 1N HCl, twice with saturated $NaHCO_3$ and once with brine. The organic layers was dried with $Na_2SO_4$ and filtered, and the filtrate was concentrated to dryness in vacuo. The desired silylated product N-|2-deoxy-|3,4,6-tris-O-|(1,1-dimethylethyl) dimethylsilyl|-2-||(9H-fluoren-9-ylmethoxy)carbonyl| amino|-β-D-glucopyranosyl|-9H-purin-6-yl|-dibenzamide was isolated by silica gel chromatography using $CH_2Cl_2$ and 0.5% to 1% $CH_3OH/CH_2Cl_2$. The appropriate fractions were collected, evaporated to dryness, and lyophilized from 1,4-dioxane. This yielded 0.059 g of product (81%). $^1$H NMR: ($CDCl_3$): adenine aromatic 8.46 (s, 1H), adenine aromatic 8.33 (s, 1H), anomeric H-1 5.97 (d, 1H). FAB-MS: m/z 1069 for (M+1))$^+$. Microanalysis: calculated for $C_{58}H_{75}N_6O_9Si_3$-(two molecules of 1,4-dioxane, $C_4H_8O_2$) C 64.77, H 7.16, N 7.55; found: C 64.37, H 7.34, N 7.63.

f) To 2.32 g (2.17 mmol) of N-|2-deoxy-|3,4,6-tris-O-|(1,1-dimethylethyl)dimethylsilyl|-2- ||(9H-fluoren-9-ylmethoxy)carbonyl|-amino|-β-D-glucopyranosyl|-9H-purin-6-yl|dibenzamide was added 9 mL of distilled $CH_2Cl_2$ and 9 mL of $CH_3OH$. The resultant solution was cooled to −5° C. and 0.76 g (3.25 mmol) of CSA was added. The reaction mixture was stirred for 2 h before dilution with $CHCl_3$ and extraction with $H_2O$ twice, with saturated, aqueous $NaHCO_3$ once, with $H_2O$ once again, and finally with brine. The organic layer was dried over $Na_2SO_4$ and filtered. The filtrate was concentrated in vacuo to a white foam. This foam was purified by elution from a silica gel flash column eluted with $CHCl_3$ and 1 to 2% $CH_3OH/CHCl_3$. Thus was obtained 1.68g (81%) of the desired primary alcohol, N-|2-deoxy- |3,4-bis-O-|( 1,1-dimethylethyl)dimethylsilyl|-2-|[(9H-fluoren-9-ylmethoxy) carbonyl|amino|-β-D-glucopyranosyl-9H-purin-6-yl| dibenzamide. $^1$H NMR: ($CDCl_3$): adenine aromatic 8.51 (s, 1H), adenine aromatic 8.33 (s, 1H), anomeric H-1 5.93 (d, 1H). FAB-MS: m/z 955 for (M+1)$^+$.

g) To 0.50 g (0.524 mmol) of N-|2-deoxy-|3,4-bis-O-|(1, 1-dimethylethyl)dimethylsilyl|-2- |[(9H-fluoren-9-ylmethoxy)carbonyl|-amino|- β-D-glucopyranosyl-9H-purin-6-yl|dibenzamide was added 0.006 g (0.050 mmol) of KBr, 0.009 g (0.027 mmol) of (n-Bu)$_4$NHSO$_4$, and 20 mL of distilled $CH_2Cl_2$. The reaction mixture was cooled to −4° C. with stirring and 0.0008 g (0.0052 mmol) of TEMPO was added. To this mixture was added in 3 portions separated by 10 min a solution containing 0.47 mL of 1.24M NaClO and 0.50 mL saturated $NaHCO_3$. At this point, the temperature was raised to 0° C. and the reaction was stirred for 2 h. At this point, the reaction was terminated by dilution with $CHCl_3$ (50 mL) and the organic solution was twice extracted with $H_2O$. The organic layers were combined, washed with brine, dried with $MgSO_4$, filtered and concentrated to dryness in vacuo.

The resulting opaque residue was dissolved in 4.6 mL of tert-butyl alcohol and 4.6 mL of $H_2O$. To this stirred solution was added 0.62 g (4.46 mmol) of $NaH_2PO_4$ and 2.36 mL (22.27 mmol) of 2-methyl-2-butene. To this solution was added 0.50 g (5.53 mmol) of $NaClO_2$. This mixture was stirred at room temperature for 30 min. At this time, the reaction mixture was poured into a mixture of EtOAc (50 mL) and $H_2O$ acidified to pH=2 with 10% (wt/vol) aqueous citric acid. The layers were separated and the organic layer was twice extracted with $H_2O$. The organic layers were combined, washed with brine, dried with $MgSO_4$, filtered and concentrated in vacuo to a white foam residue. This white foam was purified by silica gel flash column chromatography eluted with $CHCl_3$ and 1 to 4% $CH_3OH/CHCl_3$. The combined fractions were collected, evaporated, and lyophilized from dioxane and the desired adenine building block, 1- |6-|bis(phenylcarbonyl)amino|-9H-purin-9-yl|-1, 2-dideoxy-3,4-bis-O-||(1,1-dimethylethyl)dimethylsilyl|-2- ||(9H-fluoren-9-ylmethoxy)-carbonyl|amino|-β-D-glucopyranuronic acid was obtained in 74% yield (0.38 g). $^1H$ NMR: ($CD_3OD$): adenine aromatic 9.06 (s, 1H), adenine aromatic 8.47 (s, 1H), anomeric H-1 6.20 (d, 1H), t-butylsi 0.99 (s, 9H), t-butylSi 0.85 (s, 9H), $(CH_3)Si$ 0.22 (s, 3H), $(CH_3)Si$ 0.21 (s, 3H), $(CH_3)Si$ 0.11 (s, 3H), $(CH_3)Si$ −0.01 (s, 3H). FAB-MS: m/z 969 for $(M+1)^+$. Microanalysis: calculated for $C_{44}H_{56}N_4O_9Si_2$-(2 molecules of 1,4-dioxane, $C_4H_8O_2$) C 62.91,H 6.68, N 7.34; found: C 63.09, H 5.86, N 7.10.

EXAMPLE 4A

Synthesis of Guanine Building Block a) To 7.68 g of 2-acetylamino-6-hydroxypurine suspended in 400 mL of dry acetonitrile was added 20 mL of bis-silylacetamide (BSA); the mixture was heated to reflux under inert and dry atmosphere for 30 minutes. At this time, to the cooled mixture was added 8.86 g of 2-deoxy-2-|(trifluoroacetyl)amino|-β-D-glucopyranose-1,3,4,6-terraacetate and 7.72 mL of trimethylsilyl trifluoromethanesulfonate. The mixture was heated to reflux under inert atmosphere for 12 hours. At this time, the clear solution was concentrated to 100 mL volume, before the addition of 200 mL 5% (wt.vol) $NaHCO_3$ and 400 mL of EtOAc. The resulting suspension was filtered and washed with EtOAc through celite. The aqueous layer was separated and the organic layer was extracted twice with saturated $NaHCO_3$, brine, and dried with $MgSO_4$. Upon filtration and evaporation in vacuo, the resulting residue was chromatographed on silica gel eluted with 5/95 $CH_3OH/CHCl_3$. The product, N-|7-|3,4,6-tris-O-acetyl-2-deoxy-2-|(trifluoroacetyl)amino|-β-D-glucopyranosyl|-6,9-dihydro-6-oxo-1 H-purin-2-yl|-acetamide, eluted first (3.11 g, 27%): $^1H$ NMR (DMSO-d6) δH-8 8.39 (br s (broad), 1H), H-1' 6.09 (br, 1H); $^{13}C$ NMR (DMSO-d6) 6 158.0, 151.8, 147.6, 144.1, 110.8. This was followed by the coupling product, N-|9-|3,4,6-tris-O-acetyl-2-deoxy-2-|(trifluoroacetyl) amino-β-D-glucopyranosyl|-6,9-dihydro-6-oxo-1H-purin-2-yl|-acetamide (4.97 g, 43%). $^1H$ NMR (DMSO-d6) δ H-8 8.19 (br, 1H), H-1' 5.93 (s 1H); $^{13}C$ NMR (DMSO-d6) δ 154.6, 148.6, 148.1, 138.5, 120.3.

b) To 14.56 g (25.35 mmol) of N-|9-|3,4,6-tris-O-acetyl-2-deoxy-2-|(trifluoroacetyl)amino|-β-D-glucopyranosyl|-6,9-dihydro-6-oxo 1H-purin-2-yl|-acetamide was added a solution composed of 45 mL of $Et_3N$, 225 mL of $CH_3OH$, and 180 mL of $H_2O$. This solution was stirred at room temperature for 12 hours. At this time, the solution was concentrated to dryness in vacuo. The residue was recrystallized from $H_2O$ yielding a white powder (7.2 g, 69%). To 7.08 g of this white powder was added 140 mL of 30% (wt/vol) $NH_4OH$, and the reaction mixture was stirred for 15 hours at room temperature. The reaction mixture was then concentrated to dryness in vacuo. To the residue was added $H_2O$ and the mixture was frozen and lyophilized to a white powder yielding 9-(2-amino-2-deoxy-β-D-glucopyranosyl) guanine quantitatively. FAB-MS: m/z 313 for $(M+1)^+$.

c) To 3.31 g (10.61 mmol) of 9-(2-amino-2-deoxy-β-D-glucopyranosyl) guanine was added 72 mL of $H_2O$. To this solution was added a 100 mL 1,4-dioxane solution containing 4.65 g (13.79 mmol) of N-(9-fluorenylmethoxycarbonyloxy)succinimide. This resulted in a cloudy mixture. To this system was added 0.58 g (6.90 mmol) of $NaHCO_3$. This mixture was stirred for 12 hours at room temperature. At this time, TLC indicated the consumption of starting material and the mixture was concentrated in vacuo to a dry residue. This residue was stirred for 3 hours in 310 mL of $Et_2O$ and 145 ml of $H_2O$. The suspension was then filtered and the solid dried in a vacuum oven for 12 hours at 40° C. Thus was obtained 4.28 g (76%) of 9-(2-deoxy-2-||(9H-fluoren-9-ylmethoxy)carbonyl|amino|-β-D-glucopyranosyl)guanine. $^1H$ NMR: (DMSO-$δ_6$): guanine H-8 7.72 (s, 1H), anomeric H-1 5.37 (d, 1H), Fmoc-methine 4.05 (m, 1H). FAB-MS: m/z 535 for $(M+1)^+$.

d) To 2.85 g (5.34 mmol) of 9-(2-deoxy-2-||(9H-fluoren-9-ylmethoxy) carbonyl|amino|-β-D-glucopyranosyl) guanine was added dry pyridine and the resulting solution was evaporated. This procedure was repeated twice. To the residue was then added 100 mL of pyridine. To this solution was added 6.8 mL of chlorotrimethylsilane. This reaction mixture was stirred at room temperature for 10 minutes. At this time, additional chlorotrimethylsilane (1.44 mL, 64.8 mmol total) was added. The reaction mixture was stirred at room temperature for an additional 90 minutes. At this time, 2.69 mL (16.22 mmol) of isobutyric anhydride was added and the resultant solution was stirred at room temperature for 1.5 hours at which time TLC indicated the complete conversion of the starting material into product. The reaction mixture was quenched by cooling to 0° C. before addition of 60 mL of cold saturated $NaHCO_3$. This two phase system was stirred for an additional 30 minutes at which time the mixture was extracted twice with EtOAc. The EtOAc layer was concentrated to an oil in vacuo. The residue was dissolved acetonitrile and toluene and concentrated in vacuo; this procedure was repeated once more resulting in a yellow solid. The yellow solid was partitioned between a two phase solvent mixture composed of 200 mL of $H_2O$ and 500 mL of $CHCl_3$ / ethanol (3 to 2 vol/vol). The aqueous layer was extracted twice more with the solvent mixture of $CHCl_3$ / ethanol (3 to 2 vol/vol). The combined organic extracts were evaporated in vacuo and the residue was dissolved in a solvent mixture composed of 40 mL of acetonitrile, 40 mL of acetic acid, and 40 mL of $H_2O$. After 15 minutes, the mixture was evaporated to dryness yielding a slightly yellow solid. This solid was chromatographed on a silica gel drip column eluted with a quaternary solvent system composed of EtOAc / $CH_3CN$ / $CH_3OH$ / $H_2O$ (70/10/5/5). In this manner it was possible to isolate 2.44 g (75%) of N-|9-|2-deoxy-2-||(9H-fluoren-9-ylmethoxy) carbonyl|amino|-β-D-glucopyranosyl|-6,9-dihydro-6-oxo-1 H-purin-2-yl|2-methylpropanamide. $^1H$ NMR: ($CD_3OD$) :guanine H-8 8.19 (s, 1H), anomeric H-1 5.85 (d, 1H), Fmoc-methine 4.10 (m, 1H), N-isobutyryl methyl 1.10 (d, 3H), 1.00 (d, 3H). FAB-MS: m/z 605 for $(M+1)^+$.

e) 4.28 grams (7.08 mmol) of N-|9-|2-deoxy-2-||(9H-fluoren-9-ylmethoxy)carbonyl|amino|-β-D-glucopyranosyl|-6,9-dihydro-6-oxo-1 H-purin-2-yl| acetamide was reacted in dry DMF with 8.0 eq (56.64 mmol) of imidazole and 4.0 eq (4.27 mmol)tert-butyldimethyldilyl chloride. After 2 hours reaction at room temperature, the solvent was evaporated in vacuo. The residue was partitioned between EtOAc and $H_2O$, acidified to pH 2 by addition of 10% (wt/vol) aqueous citric acid. The EtOAc layer was twice extracted with $H_2O$. The combined aqueous layers were back-extracted once with EtOAc. The combined EtOAc layers were then washed once each with saturated aqueous NaHCO$_3$ and brine. The solution was dried over MgSO$_4$, filtered and the filtrate concentrated in vacuo. The residue was dissolved in a minimum of CHCl$_3$ and applied to a pad of silica gel (30 mL). The impregnated gel was eluted with 100 mL of CHCl$_3$ The bis-silyl product was eluted with 7.5% CH$_3$OH/CHCl$_3$. The appropriate fractions were concentrated to a clear oil and the oil was dried under vacuum in the presence of P$_2$O$_5$ for 12 hours. To a 0.2 Molar CH$_2$Cl$_2$ solution of 2.96 g (3.56 mmol) of the bis-silyl product at 3° C. stirred under a nitrogen atmosphere was added 4.14 mL (35.60 mmol) of 2,6-lutidine and 2.05 mL (8.90 mmol) of tert-butyldimethylsilyl trifluoromethanesulfonate. Stirring was continued at 3° C. for 20 minutes before an additional portion of tBDMSOTf (2.05 mL) was added. The reaction was stirred at room temperature for 5 hours. At this time, the reaction mixture was diluted with CH$_2$Cl$_2$ and extracted once with H$_2$O acidified with 10% (wt/vol) aqueous citric acid, twice extracted with H$_2$O. The aqueous layers were back extracted once with CH$_2$Cl$_2$. The combined organic layers were washed once with saturated, aqueous NaHCO$_3$ and finally once with brine. The organic layer was dried with MgSO$_4$, filtered, and concentrated in vacuo to a white solid. This solid was loaded to a silica gel flash column and the desired silylated product, N-|9-|2-deoxy-2-||(9H-fluoren-9-ylmethoxy)carbonyl|amino|-|3,4, 6-tris-O-|(1,1-dimethylethyl) diemthylsilyl|-β-D-glucopyranosyl|-6,9-dihydro-6-oxo-1H-purin-2-yl|-2-methylpropanamide was obtained by elution of the column with 1% CH$_3$OH/CHCl$_3$: 2.54 g (75%). $^1$H NMR: (CDCl$_3$): δ H-8 8.05 (s, 1H), H-1' 5.91 (5, 1H); calculated for C$_{48}$H$_{74}$N$_6$O$_8$Si$_3$ C 60.85, H 7.87, N 8.87; found: C 61.01, H 8.03, N 8.69; FAB-MS: m/z 947 for (M+1)$^+$.

f) 5.66 g (6.00 mmol) of N-|9-|2-deoxy-2-||(9H-fluoren-9-ylmethoxy) carbonyl|amino|-|3,4,6-tris-O-|(1,1-dimethylethyl) dimethylsilyl||-β-D-glucopyranosyl|-6,9-dihydro-6-oxo-1H-purin-2-yl|-2-methylpropanamide was treated with 1.70 equivalents of camphor sulfonic acid (CSA) (2.36 g) in 25 mL of distilled CH$_2$Cl$_2$ and 25 mL of CH$_3$OH at −10° C. The reaction was stirred at 0° C. for 2 hours before quenching the reaction with saturated aqueous NaHCO$_3$ and dilution of the mixture with CH$_2$Cl$_2$. The organic layer was twice extracted wtih saturated, aqueous NaHCO$_3$; the combined aqueous layers were extracted once with CH$_2$Cl$_2$. The combined organic layers were washed with brine, dried over MgSO$_4$, filtered and the filtrate was concentrated in vacuo to a white foam. The desired primary alcohol, N-|9-|2-deoxy-2-||(9H-fluoren-9-ylmethoxy) carbonyl|amino|-|3,4,-bis-O-|(1,1-dimethyl-ethyl) dimethylsilyl||-β-D-glucopyranosyl|-6,9-dihydro-6-oxo-1H-purin-2-yl|2-methylpropanamide was sufficiently pure to carry onto the next step for oxidation: 4.70 g (94%). $^1$H NMR: (DMSO-δ$_6$): δ anomeric H-1 5.60 (d, 1H), t-butylSi 0.92 (s, 9H), t-butylSi 0.85 (s, 9H), t-butylSi 0.79 (s, 9H). FAB-MS: m/z 833 for (M+1).

g) To 0.79 g (0.95 mmoL) of N-|9-|2-deoxy-2-||(9H-fluoren-9-ylmethoxy)carbonyl|amino|-|3,4,-bis-O-|(1,1-dimethylethyl) dimethylsilyl||-β-D-glucopyranosyl|-6,9-dihydro-6-oxo-1H-purin-2-yl|2-methylpropanamide was added 0.0034 g of KBr, 0.0016 g of (n-Bu)$_4$NHSO$_4$, and 32 mL of distilled CH$_2$Cl$_2$. The reaction mixture was cooled to 0° C. with stirring and 0.0006 g of TEMPO was added. To this mixture was added in one portion a solution containing 1.09 mL of 1.04M NaClO, 1.50 mL saturated NaHCO$_3$, and 2.37 mL of H$_2$O. The reaction was stirred for 1 hour at 0° C. At this point, the reaction was terminated by dilution with CH$_2$Cl$_2$ (50 mL) and the aqueous layer was separated. The aqueous layer was extracted once with CH$_2$Cl$_2$. The combined organic layers were concentrated in vacuo.

The resulting opaque residue was dissolved in 10 mL of tert-butyl alcohol and 10 mL of H$_2$O. To this stirred solution was added 1.05 g of NaH$_2$PO$_4$ and 4.00 mL of 2-methyl-2-butene. To this solution was added 0.86 g of NaClO$_2$. This mixture was stirred at room temperature for 30 minutes. At this time, the reaction mixture was poured into a mixture of EtOAc and H$_2$O acidified to pH=2 with 10% (wt/vol) aqueous citric acid. The layers were separated and the organic layer was twice extracted with H$_2$O. The combined organic layers were combined, washed with brine, dried with MgSO$_4$, filtered and concentrated in vacuo to a white foam residue. The desired product, 1-|2-(2-methylpropanoylamino)-1,6-dihydro-6-oxo-9H-purin-9-yl|-1,2-dideoxy-2|-||(9H- fluoren-9-ylmethoxy)carbonyl| amino|-|3,4-bis-O-|(1,1-dimethylethyl)dimethyl-silyl|-β-D-gluco-pyranuronic acid was obtained by chromatography of the residue from a silica gel drip column eluted with a quaternary solvent system composed of EtOAc / CH$_3$CN / CH$_3$OH / H$_2$O (70/10/7.55 17.5) in 75% yield (0.60 g). $^1$HNMR: (DMSO-δ$_6$): anomeric H-1 5.72 (d, 1H), t-butylSi 0.91 (s, 9H), t-butylSi 0.18 (s, 6H), (CH$_3$)$_2$Si 0.17 (s, 3H), (CH$_3$)$_2$Si 0.10 (s, 3H). FAB-MS: m/z 869 for (M+Na)+.

Alternatively, the guanine building block of formula II can be prepared as set forth in Example 4B.

EXAMPLE 4B

Synthesis of Guanine Building Block a) To 5 g (17.65 mmol) of N-|6-(phenylmethoxy)-1H-purin-2-yl|-acetamide was added 150 mL of dry CH$_3$CN and 9.60 mL (38.34 mmol) of BSA and this mixture was stirred at 80° C. for 3 h. At this time, 15.65 g (33.80 mmol) of 2-deoxy-2-|(trifluoroacetyl)amino|-β-D-glucopyranose-1,3, 4,6-tetraacetate was added followed by 6.80 mL (35.30 mmol) of TMSOTf. This mixture was heated with stirring at 80° C. for 12 hours. At this time, the reaction mixture was poured into 200 mL of saturated, aqueous NaHCO$_3$ and this mixture was extracted twice with EtOAc. The combined organic layers were washed once with H$_2$O and brine before drying over MgSO$_4$. The crude product was obtained by filtration and concentration of the filtrate in vacuo to a brownish foam. The glycosylation product was obtained by silica gel column chromatography eluted with 50% to 75% EtOAc / hexanes. Appropriate fractions were collected and further purified by normal phase preparative HPLC eluting prepacked silica cartridges with 50% EtOAc/hexanes. In this manner, 1.75 g (15% yield) of the desired product, N-|6-(phenylmethoxy)-9-|3,4,6-tris-O-acetyl-2-deoxy-2-| (trifluoroacetyl)amino|-β-D-glucopyranosyl|-1H-purin-2-yl|acetamide, was isolated. $^1$H NMR: (CDCl$_3$): guanine H-8 8.42 (s, 1H), anomeric H-1 6.19 (d, 1H), benzyl methylene 5.62 (m, 2H), N-acetamide methyl 2.30 (s, 3H). FAB-MS: m/z 667 for (M+1))$^+$.

b) To a CH$_3$OH solution of N-|6-(phenylmethoxy)-9-|3, 4,6-tris-O-acetyl-2-deoxy-2-|(trifluoroacetyl) amino|-β-D-glucopyranosyl|-1 H-purin-2-yl|-acetamide is added a catalytic quantity of 10% (wt/wt) Pd/carbon. This mixture is purged several times with hydrogen gas and then stirred at room temperature under 1 atmosphere pressure of hydrogen gas. When TLC indicates the consumption of the starting material, the mixture is filtered and washed through celite; the filtrate is then concentrated to yield N-|9-|3 ,4,6-tris-O-acetyl-2-deoxy-2-|(trifluoroacetyl)amino|-β-D-glucopyranosyl|-6,9-dihydro-6-oxo- 1H-purin-2-yl|-acetamide.

c) To N-|9-|3,4,6-tris-O-acetyl-2-deoxy-2-| (trifluoroacetyl)amino|-β-D-glucopyranosyl|-6,9-dihydro-6-oxo-1H-purin-2-yl|acetamide is added a solution composed of a solution of $Et_3N$, $CH_3OH$, and $H_2O$ (1/5/4 volume ratio). This solution is stirred at room temperature for 5 h. At this time, the solution is concentrated to dryness in vacuo. The residue is treated with 30% (wt/vol) $NH_4OH$ for 72 h at room temperature. The reaction mixture is then concentrated to dryness in vacuo. The residue is dissolved in $H_2O$ and loaded to a $C_{18}$ reversed phase gel column and eluted with $H_2O$ followed by $CH_3OH$ / $H_2O$ (1/1). Appropriate fractions are collected and evaporated to dryness in vacuo to result in 9-(2-amino-2-deoxy-β-D-glucopyranosyl) guanine.

d) To a $H_2O$ solution of 9-(2-amino-2-deoxy-β-D-glucopyranosyl)guanine is added a 1,4-dioxane solution containing 1.2 eq of N-(9-fluorenylmethoxy-carbonyloxy)-succinimide. This results in a cloudy mixture. To this system is added 0.65 eq $NaHCO_3$. This mixture is stirred for 12 h at room temperature. When TLC indicates the consumption of starting material, the mixture is concentrated in vacuo to a dry residue. This residue is stirred for 18 h in excess $Et_2O$ and $H_2O$. The suspension is then filtered and the solid dried in a vacuum oven for 12 h. The desired N-Fmoc protected amino sugar, 9-(2-deoxy-2-||9H-fluoren-9-ylmethoxy) carbonyl|amino|-β-D-glucopyranosyl)guanine will be obtained.

e) To 9-(2-deoxy-2-||(9H-fluoren-9-ylmethoxy)carbonyl| amino|-β-D-glucopyranosyl)guanine is added dry pyridine and the resulting solution is evaporated. This procedure is repeated twice. The residue is then dissolved in pyridine. To this solution is added 6 eq of chlorotrimethylsilane. This reaction mixture is stirred at room temperature for 40 min. At this time, 5 eq of acetyl chloride is added and the resultant solution is stirred at room temperature until TLC indicates the complete conversion of the starting material into product. The reaction mixture is quenched by cooling to 0° C. before addition of 10 mL of $H_2O$ and stirring for 1.5 h, followed by addition of 40 mL of cold saturated $NaHCO_3$. This 2 phase system is stirred for an additional 3 h at which time the mixture is extracted twice with EtOAc. The EtOAc layer is washed with brine and dried over $MgSO_4$, filtered and concentrated to dryness in vacuo. The residue is dissolved in EtOAc and this solution is washed thrice with 2 N HCl, thrice with saturated, aqueous $NaHCO_3$, once with brine and dried with $MgSO_4$, and filtered. The filtrate is evaporated to dryness. The residue is purified by elution from a silica gel chromatography column eluted with 15% $CH_3OH$ / $CHCl_3$ to yield the desired N-Fmoc protected amino sugar N-|9-|2-deoxy-2-||(9H-fluoren-9-ylmethoxy) carbonyl|amino|-β-D-glucopyranosyl|-6,9-dihydro-6-oxo-1H-purin-2-yl|acetamide.

f) The tris-triisopropylsilyl ether of N-|9-|2-deoxy-2-|[ (9H-fluoren-9-ylmethoxy)carbonyl|amino|-β-D-glucopyranosyl]-6,9-dihydro-6-oxo1-1H-purin-2-yl|-acetamide is formed by reaction of this material in dry DMF with excess imidazole and excess chlorodimethylisopropylsilane in presence of a catalytic quantity of DMAP. The product is isolated by evaporation of solvent, EtOAc and $H_2O$ by standard extraction procedures, concentration of the organic layer and silica gel column chromatography of the residue. This will result in good yields of tris-silyl ether, N-|9-|2-deoxy-2-||(9H-fluoren-9-ylmethoxy)carbonyl| amino|-3,4,6-tris-O-|(1-methylethyl)dimethylsilyl||-β-D-glucopyranosyl|-6,9-dihydro-6-oxo-1H-purin-2-yl| acetamide.

g) N-|9-|2-deoxy-2-||(9H-fluoren-9-ylmethoxy) carbonyl|amino|-|3,4,6-tris-O-|(1-methylethyl) dimethylsilyl||-β-D-glucopyranosyl|-6,9-dihydro-6-oxo-1H-purin-2-yl|acetamide is transformed to the guanine building block 1-|2-(acetylamino)-1,6-dihydro-6-oxo-9H-purin-9-yl|-1,2-dideoxy-2-||(9H-fluoren-9-ylmethoxy) carbonyl|amino|-|3,4-bis-O-|(1-methylethyl)-dimethylsilyl||-β-D-glucopyranuronic acid according to the procedures previously described.

EXAMPLE 5

Synthesis of Dimer and Trimer of Formula I a) To 0.13 g (0.20 mmol) of cytosine building block 1,2-dideoxy-1-|1,2-dihydro-2-oxo-4-|(phenylcarbonyl) amino|-1-pyrimidinyl|-|3,4-bis-O-|triethylsilyl|-2-||(9H-fluoren-9-ylmethoxy)carbonyl|amino|-β-D-glucopyranuronic acid was added 2 mL of DMF. To this solution was added 0.037 mL (0.31 mmol) of benzylbromide and 0.060 g (0.72 mmol) of $NaHCO_3$. This mixture was stirred for 3.5 h. At this time the solvent was removed in vacuo and the residue was dissolved in EtOAc. The EtOAc solution was extracted twice with $H_2O$, followed by washing with brine, drying with $MgSO_4$ and filtration. The filtrate was concentrated to dryness and the residue was chromatographed on silica gel eluted with 2% $CH_3OH/CHCl_3$ by which was obtained in 75% yield (0.108 g) of the desired benzyl 1,2-dideoxy-1-|1,2-dihydro-2-oxo-4-| (phenylcarbonyl)amino|-1-pyrimidinyl|-|3,4-bis-O-triethylsilyl|-2-||(9H-fluoren-9-ylmethoxy)-carbonyl| amino|-β-D-glucopyranuronate. 1H NMR: ($CDCl_3$): cytosine-H-6 8.21 (d, 1H), anomeric H-1 5.97 (d, 1H), benzyl $CH_2$ 4.59 (s, 2H). FAB-MS: m/z 703 for $(M+1))^+$.

b) To 0.030 g (0.043 mmol) of benzyl 1,2-dideoxy-1-|1, 2-dihydro-2-oxo-4-|(phenylcarbonyl)amino|-1-pyrimidinyl|-|3,4-bis-O-|triethylsilyl|-2-||(9H-fluoren-9-ylmethoxy)carbonyl|amino|-β-D-gluco-pyranuronate was added 0.50 mL of 20% piperidine in DMF. This solution was stirred at room temperature for 20 min before concentration of the reaction mixture to dryness in vacuo. The residue was redissolved in 1 mL of DMF and concentrated again to dryness in vacuo three times. In a separate ependorf vial was added 1,2-dideoxy-1-|1,2-dihydro-2-oxo-4-| (phenylcarbonyl)amino|-1-pyrimidinyl|-|3,4-bis-O-|triethylsilyl|-2-||(9H-fluoren-9-ylmethoxy)carbonyl| amino|-β-D-glucopyranuronic acid (0.046 g (0.055 mmol), 0.30 mL DMF, 0.019 mL (0.11 mmol) of DIPEA (diisopropylethylamine), and lastly 0.019 (0.050 mmol) of HATU (|O-(7-azabenzotriazol-1-yl)-1,1,3,3-tetramethyluronium hexafluorophosphate|). The components in the ependorf were mixed thoroughly and transferred after 1 min to the flask containing the first residue; the ependorf vial was rinsed with 0.3 mL of fresh DMF and that DMF was added to the reaction mixture. The reaction mixture was stirred at room temperature for 2 h. At this time, the reaction mixture was concentrated in vacuo and the residue was loaded to a silica gel flash column eluted with 2 to 4% $CH_3OH/CHCl_3$ by which was obtained 0.042 g of the desired cytosine-cytosine dimer (76%). $^1H$ NMR: $CD_3OD$): 1-cytosine-H-6 8.16 (d, 1H), 2-cytosine-H-6 8.4 (d, 1H), 1st cytosine anomeric H-1 5.91 (d, 1H), 2nd cytosine anomeric H-1 5.90 (d, 1H), benzyl $CH_2$ 5.23 (s, 2H). FAB-MS: m/z 1303 for $(M+1)^+$.

c) To 0.043 g (0.033 mmol) of the cytosine-cytosine dimer (of Example 5b) was added 0.50 mL of 20% piperidine in DMF. This solution was stirred at room temperature for 20 min before concentration of the reaction mixture to dryness in vacuo. The residue was redissolved in 1 mL of DMF and concentrated again to dryness in vacuo three times. In a separate ependorf vial was added 1.2-dideoxy-1-|1.2-dihydro-5-methyl|-2,4-dioxo-1-pyrimidinyl)-2-||(9H-fluoren-9-ylmethoxy)carbonyl|amino|-|3,4-bis-O-|triethylsilyl|-β-D -glucopyranuronic acid (0.049 g (0.066 mmol), 0.30 mL DMF, 0.023 mL (0.132 mmol) of DIPEA, and lastly 0.024 g (0.063 mmol) of HATU. The components in the ependorf were mixed thoroughly and transferred after 1 min to the flask containing the first residue; the ependorf vial was rinsed with 0.3 mL of fresh DMF and the rinse was added to the reaction mixture. The reaction mixture was stirred at room temperature for 70 min. At this time, the reaction mixture was concentrated in vacuo and the residue was loaded to a silica gel flash column eluted with 2 to 3.5% $CH_3OH/CHCl_3$ by which was obtained 0.045 g of the desired cytosine-cytosine-thymine trimer (75%). $^1$H NMR: $CD_3OD$): 1-cytosine-H-6 8.40 (d, 1H), 2-cytosine-H-6 8.27 (d, 1H), 1st cytosine anomeric H-1 6.25 (d, 1H), 2nd cytosine anomeric H-1 6.13 (d, 1H), thymine anomeric H-1 5.82 (d, 1H), benzyl $CH_2$ 5.23 (s, 2H). FAB-MS: m/z 1814 for $(M)^+$.

EXAMPLE 6

Synthesis of Oligomer: $H_2N$-Lys-TCTCTCTCCTTCT-H (SEQ ID No: 3)

To a freshly silylated solid phase peptide micro reactor 50 mg of 0.1 mmol/g (5.0 mmol) charged Fmoc-Lys(e-Boc)-Knorr-BHA-polystyrene resin was added. The Fmoc protecting group was removed by three successive treatments with 0.25 mL of 20% piperidine in DMF for one min, seven min and seven min durations. After each treatment, the resin was purged of the solution; after the third treatment, the resin was thrice washed with DMF and thrice with $CH_2Cl_2$. To the micro reactor was added 0.025 mmol of the thymine building block, followed by 0.35 mL of dry DMF and 0.0086 mL (0.05 mmol) of DIPEA and finally 8.6 mg (0.022 mmol) of HATU in such a fashion that this solution did not come in contact with the resin-bound free amine until one minute after addition of the HATU reagent. The resin was then gently shaken for 20 min before purging the reactor of solvent; the resin was thrice washed with DMF and thrice with $CH_2Cl_2$. Subsequent couplings were performed by repetition of the same Fmoc-deprotection and coupling procedures. Optional capping was performed by treatment with 5% (vol/vol) acetic anhydride in DMF for 5 min followed by washing the resin with DMF and $CH_2Cl_2$, three times each.

After completion of the coupling sequences, the final Fmoc group was removed in the same manner as described above. The free amino resin was then treated with TFA/$CH_2Cl_2$ (1:1) for 1 hour. The resin was removed from the solvent by filtration through cotton and the filtrate was concentrated to dryness in vacuo. The residue was suspended in $Et_2O$ and then centrifuged; the $Et_2O$ layer was discarded. This $Et_2O$ procedure was repeated twice further. The residual solid was then treated for 12 h at room temperature for 0.3 mL of 30% (wt/vol) $NH_4OH$. At this time, the reaction mixture was concentrated to dryness in vacuo. At this time, the reaction mixture was concentrated to dryness in vacuo. The residue was treated with 1 mL of 1.0 molar tetrabutylammonium fluoride in tetrahydrofuran for 12 hours at room temperature. At this time, 0.3 mL of aqueous 0.5 molar $NH_4OAc$ (ammonium acetate) was added and the mixture was concentrated in vacuo. The residue was diluted to a volume of 2.5 mL by addition of $H_2O$ and this solution was loaded to a washed NAP-25 column (Pharmacia). After the penetration of the solution into the solid phase of the column, elution of the desalted and crude product was effected with 3.5 mL of $H_2O$. This was collected and lyophilized. The residue was dissolved in $H_2O$ and purified by reversed phase HPLC: (VYDAC-C4 10 μ22×250 mm preparative column, 265 nm detection, 1.5 mL/min flow rate, elution with 20% $CH_3CN/H_2O$, 0.2% HFBA (heptafluorobutyric acid) for 0–15 min, then 15–20 min a linear gradient to 20% $CH_3CN/H_2O$, 0.1% TFA). The appropriate fractions were combined and lyophilized. The purified oligomer was homogenous as measured by analytical HPLC using another elution conditions: Waters μ Bondpak $C_{18}$ 3.9×300 mm eluted with a 20 min linear gradient from 20% $CH_3CNIH_2O$ to 20% $CH_3CN/H_2O$, 0.1% TFA at 1.5 mL/min flow rate. The identity of the purified oligomer was confirmed by MALDI-TOF mass spectrometry as 3737 for $(M+1))^+$.

EXAMPLE 7

Hybridization Properties of Oligomer Thermal Melting Studies

Absorbance versus temperature curves were measured at 260 nm using a Cary 3 spectrophotometer equipped with an electrothermal temperature controller and interfaced with an IBM PS2/50 Z computer. Oligonucleotide concentration was 1.4 μM and the buffer contained 100 mM NaCl 10 mM sodium phosphate, and 0.1 mM EDTA, pH 7. Tm values were determined from the maxim of first derivative plots using the Reducep program (Koerber, S. C.; Fink, A. L., *Analytical Biochemistry* 1987, 165, 75–87) which utilizes the Savitzky-Golay algorithm (Savitzky, A.; Golay, M. J. E. *Analytical Chemistry* 1964, 36, 1627–39) thermodynamic constants were obtained from fits of data to a two-state model with linear sloping baselines (Petersheim, M.; Turner, D. H. *Biochemistry* 1983, 22, 256–263).

TABLE I

| HIV gag sequence | | up | | down | |
|---|---|---|---|---|---|
| 5'-TCTCTCTCCTTCT-3' | DNA | 44.2 | | 43.4 | |
| 3'-AGAGAGAGGAAGA-5' | DNA | | | | |
| 5'-TCTCTCTCCTTCT-3' | DNA | 55.1 | | 54.8 | |
| 3'-AGAGAGAGGAAGA-5' | RNA | | | | |
| $H_2N$—Lys TCTCTCTCCTTCT-H (SEQ ID NO: 3) | Example 6 | 19.2 | 67.2 | 18.7 | 66.4 |
| 5'-       AGAGAGAGGAAGA-3' | DNA | | | | |
| $H_2N$—Lys TCTCTCTCCTTCT-H (SEQ ID NO: 3) | Example 6 | 54.1 | | 53.7 | |
| 5'-       AGAGAGAGGAAGA-3' | RNA | | | | |

Table I Numbers are for melting temperature (Tm's) in degrees Celsius. Total strand concentration was 3 mM in a buffer of 100 mM NaCl, 10 mM sodium phosphate, 0.1 mM EDTA, pH 7.0. "Up" indicates the melting temperature; "Down" indicates the annealing temperature.

As shown in Table I, the binding of oligonucleotide of formula I, Example 6 (H₂N-Lys-TCTCTCTCCTTCT-H) (SEQ ID No:3) to RNA and DNA is compared to the binding of DNA to DNA and RNA to DNA. A higher melting temperature indicates a tighter association of the indicated duplex. From the data in Table I, it is clear that an oligonucleotide of formula I (Example 6) binds with greatest affinity to a complementary segment of RNA in a n antiparallel fashion (carboxamide terminal of Example 6, binding to the 5' end of an oligo). This strength in binding is similar to that of DNA binding activity. The melting temperatures determined by heating and cooling (up and down, respectively) are similar. The similarity of a melting temperature despite the direction of the change in temperature during these measurement is indicative of an association between two oligomers.

EXAMPLE 8

Base-Pairing Specificity of Oligomer Thermal Melting Studies

Conditions: 100 mM NaCl, 10 mM sodium phosphate, 0.1 mM EDTA, pH 7.

Melting Temperatures (Tm's) in ° C

In order to test the selectivity of binding, the binding of the same oligonucleotide of Example 6 was investigated for RNA targets sequences containing a single base that is not complementary to the oligonucleotide of formula I base sequence. The results of these investigations are shown in Table II. A decrease in the melting temperature indicates that the oligomer of formula I binds a complementary sequence with greater affinity than to a sequence that is not perfectly complementary. A decrease in binding affinity due to the presence of base mismatches is termed selectivity. As is seen from the data in Table II, the oligomer of Example 6 binds in a selective fashion in the Watson-Crick complementary base-pairing manner.

TABLE II

| | ramp up (down): °C |  |
|---|---|---|
| 5'-r (AGAGAGAGGAAGA)-3' H₂N—Lys TCTCTCTCCTTCT-H (Example 6) | 53.3 | (53.2) |
| 5'-r (AGAGAGAAGAAGA)-3' H₂N—Lys TCTCTCTCCTTCT-H (Example 6) | 45.7 | (44.8) |
| 5'-r (AGAGAGACGAAGA)-3' H₂N—Lys TCTCTCTCCTTCT-H (Example 6) | 43.2 | (42.9) |
| 5'-r (AGAGAGAUGAAGA)-3' H₂N—Lys TCTCTCTCCTTCT-H (Example 6) | 48.3 | (47.6) |

Table II Numbers are for melting temperature (Tmn's) in degrees Celsius. Total strand concentration was 3 μM. Strands are bound in the antiparallel orientation. Numbers in parenthesis indicate the annealing temperature.

EXAMPLE 9

Cell-Based Antisense Assay

Antisense molecules have been demonstrated to reduce levels of the enzyme tyrosinase in melanocytes by the methods described below. These antisense molecules have potential utility for treating several diseases of hyperpigmentation (hypermelanosis) including, but not limited to cafe au lait macules, nevus spilus, post inflammatory mealnosis (exanthems, drug eruptions) and scleroderma.

A commonly used line of mouse melanoma cells (for example, B-16) is raised in cell culture plates using Dulbecco's Modified Eagle's Medium supplemented with 10% fetal bovine serum and 50 μg/ml gentamicin. To initiate an experiment, antisense and control oligonucleotides are added to low density (that is, sub-confluent) cell cultures, then treatment is continued for several days. Cells are then rinsed with saline, collected by scraping, then cells are extracted and analyzed for levels of protein by the Bradford method (Bradford, M. M. *Anal. Biochem.* 1976, 72: 248).

Levels of the target enzyme tyrosinase from a constant amount of extracted protein is measured essentially as described by a published procedure (Pomerantz, S. H. *J. Biol. Chem.* 1966, 241: 161). Briefly, extracts are incubated with tyrosine and the cofactor DOPA (3,4-dihydroxyphenylalanine.) The tyrosine is tritium labeled at the 3 and 5 positions such that tyrosinase activity is measured by the amount of tritiated water that is produced. Tritiated water is quantitated by liquid scintillation counting. The purpose of the tyrosinase assay is to establish the potency of each antisense molecule by allowing us to calculate the concentration necessary to cause 50% inhibition of tyrosinase levels ($IC_{50}$).

To control for effects due to nonspecific toxicity, melanoma cells are seeded into 96-well plates at low density, then allowed to grow in the presence of antisense and control oligonucleotides for several days. Cell proliferation is assayed by the widely used tetrazolium dye procedure (Mosmann, T. *J. Immunol. Meth.* 1983,65, 55). The concentration of each oligonucleotide producing 50% inhibition of growth rate is compared to the concentration of that oligonucleotide which produces 50% inhibition of tyrosinase level. Antisense effects are indicated by the following conditions: a) active oligonucleotides are complementary in sequence to the target messenger RNA, b) sense and mismatched controls are less active than fully matched antisense oligonucleotides, c) tyrosinase activity is inhibited by concentrations of antisense oligonucleotides which do not suppress cell growth.

The selectivity of the antisense mechanism of these antisense molecules is determined by measuring the enzyme levels of two non-targetted cellular enzymes: alkaline phosphotase and tyrosine kinase.

---

We claim:

1. An oligomer of formula

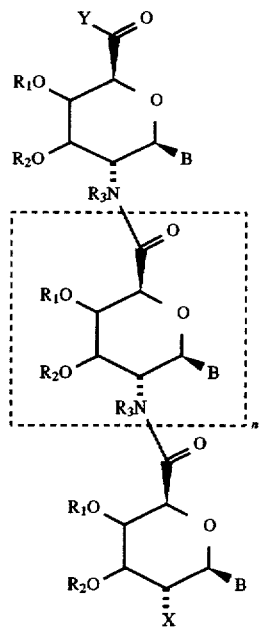

wherein $R_1$, $R_2$ and $R_4$ are independently hydrogen, lower alkyl or acyl;

$R_3$ is hydrogen or lower alkyl;

B is a nucleobase or a protected nucleobase, such that said oligomer has a sequence of bases complementary to a selected RNA;

n is 5 to 30;

X is $NR_3R_4$; and

Y is $OR_3$, or $NHR_3$;

or pharmaceutically acceptable salts thereof.

2. The oligomer of claim 1, wherein $R_1$, $R_2$ and $R_4$ are independently hydrogen, methyl, ethyl or acetyl.

3. The oligomer of claim 2, wherein $R_1$, $R_2$ and $R_4$ are independently hydrogen or acetyl.

4. The oligomer of claim 1, wherein $R_3$ is hydrogen or methyl.

5. The oligomer of claim 1, wherein $R_3$ is hydrogen.

6. The oligomer of claim 1, wherein B is thymine, cytosine, adenine, guanine, uracil, N-benzoylcytosine, N-acetylcytosine, N-benzoyladenine, N,N-dibenzoyladenine, N-acetylguanine or N-15 isobutyrylguanine.

7. The oligomer of claim 1, wherein n is 5 to 20.

8. The oligomer of claim 1, wherein X is $NH_2$ or NHAc wherein Ac is acetyl.

9. The oligomer of claim 8, wherein X is $NH_2$.

10. The oligomer of claim 1, wherein Y is hydroxy, $OCH_3$, $NHCH_3$, or $NH_2$.

11. The oligomer of claim 10, wherein Y is hydroxy or $NH_2$.

12. The oligomer of claim 6, wherein B is thymine, cytosine, adenine, guanine or uracil.

13. The oligomer of claim 1, wherein $R_1$ and $R_2$ are independently hydrogen, methyl, ethyl or acetyl, $R_3$ is hydrogen or methyl, B is thymine, cytosine, adenine, guanine, uracil, N-benzoylcytosine, N-acetylcytosine, N-35 benzoyladenine, N,N-dibenzoyladenine, N-acetylguanine or N-isobutyrylguanine; n is 5 to 20; X is $NH_2$ or NHAc wherein Ac is acetyl and Y is hydroxy, $OCH_3$, $NH_2$ or $NHCH_3$.

14. The oligomer of claim 13, wherein $R_1$ and $R_2$ are independently hydrogen or acetyl, $R_3$ is hydrogen, X is $NH_2$, Y is hydroxy or $NH_2$, n is 5–15 and B is thymine, cytosine, adenine, guanine or uracil.

15. An oligomer of formula

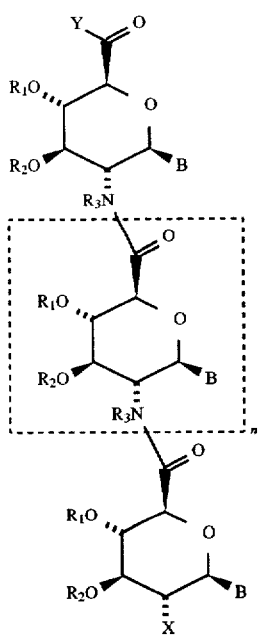

wherein
- $R_1$, $R_2$ and $R_4$ are independently hydrogen, lower alkyl or acyl;
- $R_3$ is hydrogen or lower alkyl;
- B is a nucleobase or a protected nucleobase, such that said oligomer has a sequence of bases complementary to a selected RNA;
- n is 5 to 30;
- X is $NR_3R_4$; and
- Y is $OR_3$, or $NHR_3$;

or pharmaceutically acceptable salts thereof.

16. The oligomer of claim 15, wherein $R_1$ and $R_2$ are independently hydrogen, methyl, ethyl or acetyl, $R_3$ is hydrogen or methyl, B is thymine, cytosine, adenine, guanine, uracil, N-benzoylcytosine, N-acetylcytosine, N-benzoyladenine, N,N-dibenzoyladenine, N-acetylguanine or N-isobutyryl-guanine; n is 5 to 20; X is $NH_2$ or NHAc wherein Ac is acetyl and Y is hydroxy, $OCH_3$, $NH_2$ or $NHCH_3$.

17. A pharmaceutical composition which comprises a compound of formula

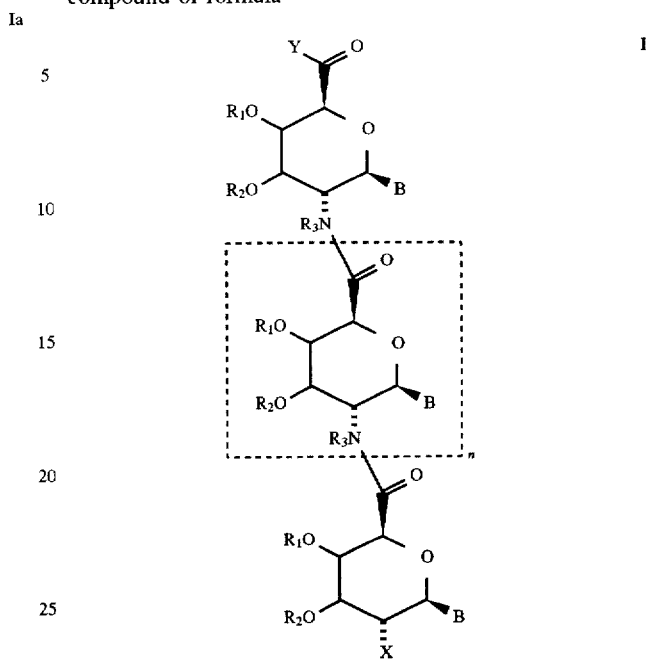

wherein
- $R_1$, $R_2$ and $R_4$ are independently hydrogen, lower alkyl or acyl;
- $R_3$ is hydrogen or lower alkyl;
- B is a nucleobase or a protected nucleobase, such that said oligomer has a sequence of bases complementary to a selected RNA;
- n is 5 to 30;
- X is $NR_3R_4$;
- Y is $OR_3$, or $NHR_3$;

or a pharmaceutically acceptable salt thereof and a pharmaceutically inert carrier.

* * * * *

UNITED STATES PATENT AND TRADEMARK OFFICE
CERTIFICATE OF CORRECTION

PATENT NO. : 5,780,607
DATED : July 14, 1998
INVENTOR(S) : Robert A. Goodnow, Jr., Steve Yik-Kai Tam It is certified that error appears in the above-identified patent and that said Letters Patent is hereby corrected as shown below:

In claim 6, column 40, line 38, delete "N-15 isobutyrylguanine." and insert -- N-isobutyrylguanine. --.

In claim 13, column 40, line 58, delete "N-35 benzoyladenine," and insert -- N-benzoyladenine, --.

Signed and Sealed this

Twenty-fourth Day of November, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

-continued

```
( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:
```

AGAAGGAGAG AGA                                                                      13

( 2 ) INFORMATION FOR SEQ ID NO:2:

```
    ( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:2:
```

AGAAGGAGAG AGA                                                                      13

( 2 ) INFORMATION FOR SEQ ID NO:3:

```
    ( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:3:
```

TCTCTCTCCT TCT                                                                      13

( 2 ) INFORMATION FOR SEQ ID NO:4:

```
    ( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:4:
```

AGAGAGAAGA AGA                                                                      13

( 2 ) INFORMATION FOR SEQ ID NO:5:

```
    ( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear
```

```
        ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:5:

AGAGAGACGA AGA                                              1 3

( 2 ) INFORMATION FOR SEQ ID NO:6:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:6:

AGAGAGAUGA AGA                                              1 3
```